US012582840B2

(12) United States Patent
Voet et al.

(10) Patent No.: US 12,582,840 B2
(45) Date of Patent: Mar. 24, 2026

(54) SYSTEM AND METHOD FOR RADIATION TREATMENT PLANNING

(71) Applicant: Elekta, Inc., Atlanta, GA (US)

(72) Inventors: Peter Voet, Atlanta, GA (US);
Chunhua Men, Atlanta, GA (US);
Spencer Marshall, Brandon, FL (US)

(73) Assignee: Elekta, Inc., Atlanta, GA (US)

( * ) Notice: Subject to any disclaimer, the term of this patent is extended or adjusted under 35 U.S.C. 154(b) by 287 days.

(21) Appl. No.: 18/315,961

(22) Filed: May 11, 2023

(65) Prior Publication Data

US 2024/0374925 A1     Nov. 14, 2024

(51) Int. Cl.
*A61N 5/10*          (2006.01)

(52) U.S. Cl.
CPC ......... *A61N 5/1031* (2013.01); *A61N 5/1045* (2013.01); *A61N 2005/1034* (2013.01)

(58) Field of Classification Search
CPC ........ A61N 5/10; A61N 5/1001; A61N 5/103; A61N 5/1031; A61N 5/1039; A61N 5/1045; A61N 2005/1034; A61N 2005/1087; A61N 2005/1089; G16H 20/40
See application file for complete search history.

(56) References Cited

U.S. PATENT DOCUMENTS

| | | | |
|---|---|---|---|
| 6,064,203 | A | 5/2000 | Bottomley |
| 6,963,771 | B2 | 11/2005 | Scarantino et al. |
| 7,317,192 | B2 | 1/2008 | Ma |

| | | | |
|---|---|---|---|
| 8,492,735 | B2 | 7/2013 | Brand |
| 9,884,206 | B2 | 2/2018 | Schulte et al. |
| 10,737,114 | B2 | 8/2020 | Gattiker et al. |
| 10,835,760 | B2 | 11/2020 | Kuusela et al. |
| 2010/0104068 | A1 | 4/2010 | Kilby et al. |
| 2013/0072742 | A1 | 3/2013 | Nord et al. |
| 2015/0202464 | A1 | 7/2015 | Brand et al. |
| 2018/0304099 | A1 | 10/2018 | Li et al. |
| 2019/0247676 | A1 | 8/2019 | Peltola et al. |

(Continued)

FOREIGN PATENT DOCUMENTS

EP          3681600          7/2020

OTHER PUBLICATIONS

Elekta AB,, Monaco Training Guide, Document ID: LTGMON0530, (2017), 1313 pgs.

(Continued)

*Primary Examiner* — Jurie Yun
(74) *Attorney, Agent, or Firm* — Schwegman Lundberg & Woessner, P.A.

(57)          ABSTRACT

A method for radiation treatment planning for delivering radiation therapy by a radiotherapy system, the method comprising: receiving a reference objective, the reference objective representing a goal to be achieved by the radiotherapy system; performing an optimisation procedure, according to the received reference objective, to determine a set of parameters, the set of parameters relating to characteristics of radiation to be delivered by the radiotherapy system, wherein the optimisation procedure comprises: optimising the set of parameters to obtain an achieved value, and responsive to the achieved value not meeting the reference objective, obtaining a relaxed objective using the achieved value and a relaxation value, and determining a configuration of the radiotherapy system using the optimised set of parameters and the relaxed objective.

18 Claims, 10 Drawing Sheets

(56) References Cited

U.S. PATENT DOCUMENTS

2021/0138267 A1    5/2021  Nord et al.
2021/0316157 A1   10/2021  Lynch et al.

OTHER PUBLICATIONS

"European Application No. 24175404.3, Extended European Search Report dated Dec. 6, 2024", (Dec. 6, 2024), 9 pgs.

Naccarato, Stefania, "Automated Planning for Prostate Stereotactic Body Radiation Therapy on the 1.5 T MR Linac", Advances in Radiation Oncology vol. 7 Issue 3, Oct. 19, 2021, 12 pgs.

SYSTEM AND METHOD FOR RADIATION TREATMENT PLANNING

FIELD

Embodiments herein relate to systems and methods for radiation treatment planning for delivering radiation therapy.

BACKGROUND

Radiotherapy or radiation therapy can be described as the use of ionising radiation to damage or destroy unhealthy cells in both humans and animals. The ionising radiation may be directed to tumours on the surface of the skin or deep inside the body. Common forms of ionising radiation include X-rays and charged particles. An example of a radiotherapy technique is Gamma Knife® or Leksell Gamma Knife® where a patient is irradiated using a number of lower-intensity gamma rays that converge with higher intensity and high precision at a targeted region (e.g., a tumour). Another example of radiotherapy comprises using a linear accelerator ("linac"), whereby a targeted region is irradiated by high-energy particles (e.g., electrons, high-energy photons, and the like). In another example, radiotherapy is provided using a heavy charged particle accelerator (e.g., protons, carbon ions, and the like).

The placement and dose of the radiation beam is accurately controlled to provide a prescribed dose of radiation to the targeted region (e.g. the tumour) and to reduce damage to surrounding healthy tissue (known as organs at risk or OARs). An aspect of treatment planning concerns determining suitable characteristics of radiation to be delivered to produce a safe and effective dose. Characteristics of radiation relate to, for example, a fluence pattern. The fluence pattern may be dependent on beam arrangements, energies, and field sizes, which are in turn related to controllable parameters (which are optimisable). By determining suitable values for those parameters, a suitable fluence pattern may be obtained. A treatment plan may be determined by a treatment planning system.

A radiation therapy treatment plan (treatment plan) comprises using an optimisation procedure to determine a set of optimum parameters that would deliver a suitable dose. The optimisation procedure may be based on clinical and dosimetric objectives and constraints. Examples of clinical and dosimetric objectives and constraints include maximum, minimum, and mean doses to a tumour and critical organs. Clinical and dosimetric objectives and constraints may be referred to as treatment-planning objectives.

The treatment planning procedure may include using a three-dimensional image of the patient to identify a target region and to identify critical organs near the tumour. The target region, area to be treated (e.g., a planned target volume (PTV)), and Organs at Risk (OARs) may be identified using segmentation. After segmentation, a dose plan may be created for the patient indicating the desirable amount of radiation to be received by the PTV (e.g., target) and/or the OARs. The PTV may have an irregular volume.

In a practical example, multiple anatomical structures (i.e., PTV, targets, and/or OARs) may be present. For example, in a head and neck treatment, there may be over 20 anatomical structures. For each structure, compliance with various treatment-planning objectives is desired. Structures and their objectives may be assigned different priorities in order to achieve a clinically acceptable plan. Determining a treatment plan to meet the various objectives is time-consuming and complex.

There is a need for improved methods and systems for generating treatment plans.

BRIEF DESCRIPTION OF FIGURES

Systems and methods in accordance with non-limiting examples will now be described with reference to the accompanying figures in which.

DETAILED DESCRIPTION

Figure 1A:
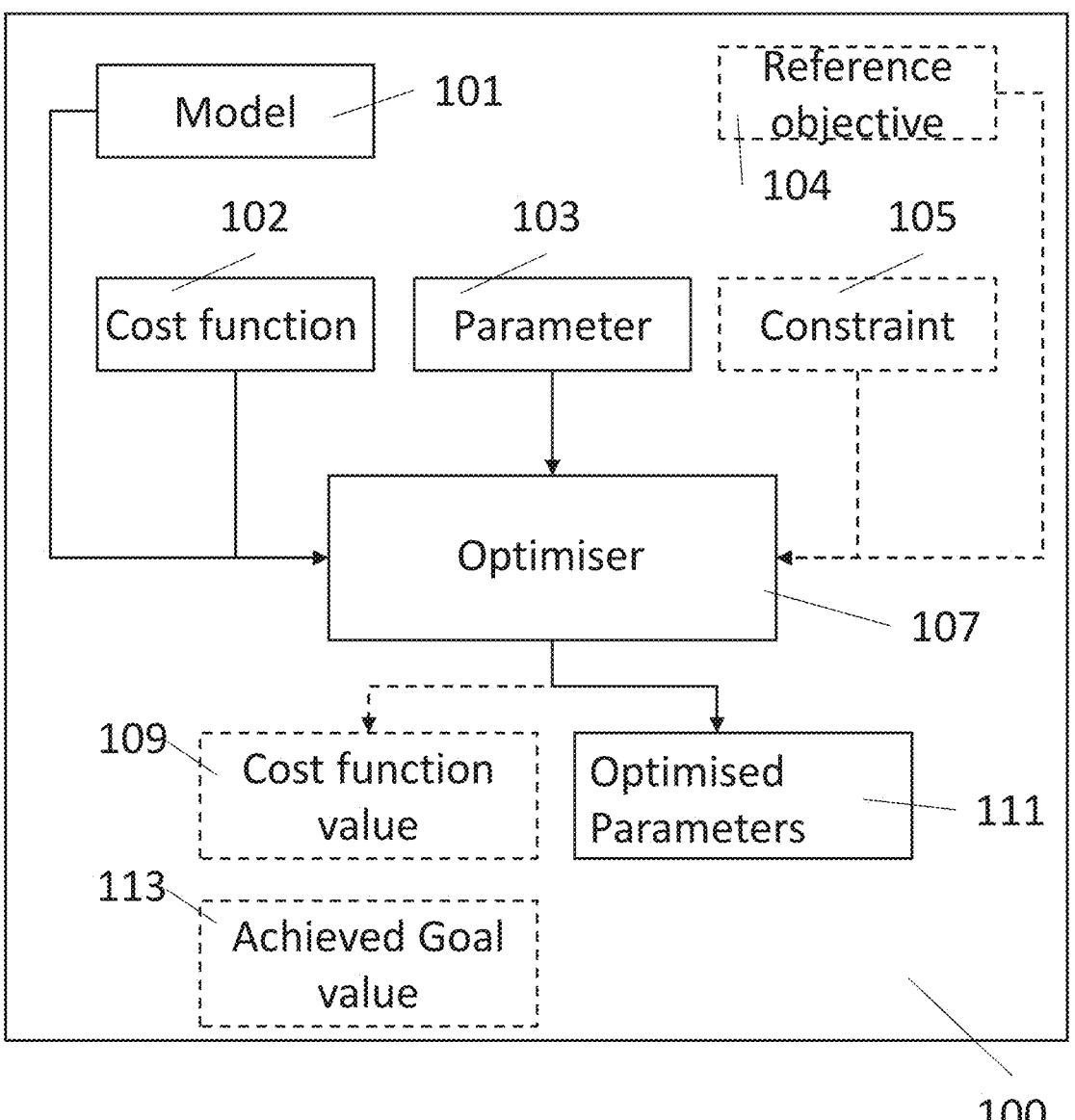
FIG. 1A shows a block diagram of an optimisation procedure according to an example.

As described above, the generation of a treatment plan may be time consuming and complex, particularly when many treatment-planning objectives are present.

Treatment planning comprises performing an optimisation procedure to optimise a number of parameters, the purpose being to provide a sufficiently high dose to the PTV while reducing the dose to the surrounding healthy tissue. By balancing the different treatment-planning objectives, for example by prioritising treatment-planning objectives that relate to the dose coverage at the PTV and then treatment-planning objectives that relate to sparing OARs, a clinically suitable plan may be obtained. By prioritising one objective over another objective, it is meant that an optimisation procedure is performed based on a first objective, and then a further optimisation procedure is performed based on a second objective having lower priority than the first objective. It is understood that throughout this procedure optimise and optimize, and their variations, may be used interchangeably.

A user (e.g., a treatment planner, dosimetrist, clinician or health care worker) may achieve a clinically suitable plan as follows. For each treatment-planning objective, the user may configure the optimiser by defining, e.g., a reference dose, reference volume, and/or cost function. An example of a treatment-planning objective may be stated as '97% of the volume of the PTV should receive at least 40 Gy'. The objective represents a goal to be achieved. The optimiser would then try to find optimised parameters that meet this goal. The solution found by the optimiser may or may not meet the desired goal (based on the anatomy, limitations of the radiotherapy machine and/or difficulty of the problem). Based on the achieved goal, optimisation may be repeated using a revised goal to be achieved. This approach is time consuming and leads to variable results, based on the user's choice of revised goal to be achieved. Furthermore, when a plurality of treatment-planning objectives is considered, this approach is repeated for each objective, making plan generation even more time consuming.

The inventors of the present disclosure have devised methods and systems that may improve the quality of a generated treatment plan and reduce the time required to generate such a plan. The methods and systems also reduce the need for user input. In particular, the inventors have devised methods and systems whereby, for each treatment-planning objective, an optimisation procedure is performed to obtain an achieved solution (achieved value). Based on whether the achieved solution meets the treatment-planning objective (reference objective), a relaxed objective is obtained (using a relaxation value) and then used in subsequent steps. The relaxed objective is less strict than the treatment-planning objective and/or the achieved solution. The relaxed objective provides an improved starting point for subsequent steps. The relaxed objective improves the likelihood of convergence in subsequent steps or the likelihood that a suitable outcome is obtained in subsequent steps.

The methods and systems herein address a technical problem arising in the field of radiotherapy treatment planning, namely, how to improve generation of a treatment plan. The method may improve the accuracy of the generated treatment plan and the speed of generation. The method also automates the generation of a treatment plan.

According to an aspect, there is provided a method for radiation treatment planning for delivering radiation therapy by a radiotherapy system, the method comprising:

receiving a reference objective, the reference objective representing a goal to be achieved by the radiotherapy system;

performing an optimisation procedure, according to the received reference objective, to determine a set of parameters, the set of parameters relating to characteristics of radiation to be delivered by the radiotherapy system, wherein performing the optimisation procedure comprises:

optimising the set of parameters to obtain an achieved value, responsive to the achieved value not meeting the reference objective, obtaining a relaxed objective using the achieved value and a relaxation value, and determining a configuration of the radiotherapy system using the optimised set of parameters and the relaxed objective.

The configuration of the radiotherapy system may be outputted for delivering radiation by the radiotherapy system.

Performing the optimisation procedure may comprise performing a first pass optimisation, first pass optimisation comprising: optimising the set of parameters to obtain a first pass achieved value, and, responsive to the first pass achieved value not meeting the reference objective, obtaining a first pass relaxed objective using the first pass achieved value and a first pass relaxation value, and determining a configuration of the radiotherapy system using the optimised set of parameters and the first pass relaxed objective.

The methods improve the generation of a treatment plan by performing optimisation (first pass optimisation) to obtain a first solution (first pass achieved value), and, in response to the first solution not meeting a desired goal (reference objective), obtaining a relaxed solution (first pass relaxed objective) using the achieved solution (first pass achieved value) and a relaxation value (first pass relaxation). The optimised parameters and the relaxed solution (first pass relaxed objective) are then used to determine a configuration of the radiotherapy system.

The relaxation value (first relaxation value) is used to modify the achieved solution (first pass achieved value), to obtain a relaxed solution (first pass relaxed objective). The relaxed solution is subsequently used to determine a configuration of radiotherapy system, without requiring further input from a user. The purpose of modifying the achieved solution using a relaxation value is to allow 'room' for subsequent steps and/or to allow a broader solution space to be accessed in subsequent steps. This improves the performance of the method, (e.g., by increasing the likelihood that the determined configuration is acceptable) and improves the chances that a treatment plan is generated, without requiring further user input.

The achieved solution relates to a quantity that is comparable to the reference objective (e.g., it has the same units and/or meaning).

From the optimised set of parameters and the relaxed solution, a configuration of the radiotherapy system is determined. The configuration may relate to an arrangement of field modifiers, for example. The determined configuration is useable by the radiotherapy system for delivering radiation therapy.

In an embodiment, the method comprises:

responsive to the first pass achieved value meeting the reference objective, determining a configuration of the radiotherapy system using the optimised set of parameters and the reference objective.

When the achieved value meets the reference objective, the reference objective is used in subsequent steps. No relaxation is applied. By using the reference objective instead of the achieved value (which meets or betters the reference objective), more room is allowed for subsequent steps.

In an embodiment, determining a configuration of the radiotherapy system using the optimised set of parameters and the first pass relaxed objective comprises:

performing an optimisation procedure using the first pass relaxed objective as an objective or a constraint.

In an embodiment, the method further comprises:

performing second pass optimisation, wherein performing second pass optimisation comprises:

responsive to the first pass achieved value meeting the reference objective, further optimising the set of parameters, according to the received reference objective, such that the radiotherapy system achieves a second pass achieved value, and obtaining a second pass relaxed objective using the second pass achieved value and a second pass relaxation value, and determining a configuration of the radiotherapy system using the further optimised set of parameters and the second pass relaxed objective.

When the first pass achieved value meets the reference objective, no relaxation is applied in first pass optimisation. Second pass optimisation is performed, and by further optimising the set of parameters, a more suitable solution is obtained. By obtaining a second pass relaxed objective that is used to determine a configuration, a broader solution space may be accessed in the determination of a configuration step. By further optimising the set of parameters in second pass optimisation, it is meant that the solution (e.g. the optimised parameters) from the first pass is used as a starting point.

In an embodiment, determining a configuration of the radiotherapy system using the further optimised set of parameters and the second pass relaxed objective comprises:

5 performing a further optimisation procedure using the second relaxed treatment-planning objective as an objective or a constraint.

In an embodiment, the set of parameters are related to the fluence pattern of the radiation to be delivered.

In an embodiment, the set of parameters comprises the weight of beamlets.

In an embodiment, determining a configuration of the radiotherapy system comprises determining an arrangement of a beam shaping apparatus.

In an embodiment, the beam shaping apparatus is a multileaf collimator (MLC).

In an embodiment, the first pass relaxation value and/or second pass relaxation value is automatically set according to a cost function. This enables the first/second pass relaxation value to be set according to the cost function being used in the optimization. For example, some cost functions may converge more slowly than others. This may improve the speed of the optimization and the suitability of the achieved value.

In an embodiment, the reference objective comprises any of a cost function, reference dose, and/or reference volume.

In an embodiment, when the reference objective comprises a reference dose, the cost function comprises any of: a Maximum dose cost function, a Mean dose cost function, a Serial cost function, and/or an equivalent uniform dose (EUD) cost function.

In an embodiment, when the reference objective comprises a reference volume, the cost function comprises any of: a Dose Volume Histogram (DVH) based cost function, a Target Penalty cost function or a Parallel cost function In an embodiment, the reference objective relates to any one or more of: a region of interest, a shell, a planned target volume (PTV), a critical structure, and an organ at risk.

In an embodiment, the first pass relaxation value is obtained relative to the first pass achieved value, and further bounded by a lower value and an upper value. This enables the first pass relaxed objective to have a more suitable value, tailored to the type of reference objective, and further improves the optimisation.

In an embodiment, the second relaxation value is smaller than the first relaxation value. This further improves the optimisation procedure. In the first pass, the optimiser has already covered a broad solution space by being constrained by the larger first relaxation value. Using a smaller second relaxation value in the second pass narrows the solution space and leads to improved optimisation.

In an embodiment the second relaxation value is between 25% to 75% of the first relaxation value. This is to further ensure that the second objective achieved by the treatment planning system lies within an acceptable range.

According to an example, there is provided a method for delivering radiation therapy by a radiotherapy system, the method comprising:

receiving a first reference objective and a second reference objective, each reference objective representing a goal to be achieved by the radiotherapy system;

for each reference objective, sequentially optimising the set of parameters according to any preceding method; and determining a configuration of the radiotherapy system using the sequentially optimised set of parameters and the first and second reference objectives.

According to another aspect, there is provided a method for radiation treatment planning for delivering radiation therapy by a radiotherapy system, the method comprising:

receiving a first reference objective and a second reference objective, each reference objective representing a goal to be achieved by the radiotherapy system;

performing first pass optimisation, according to the first reference objective and the second reference objective, to determine a set of parameters, the set of parameters relating to characteristics of radiation to be delivered by the radiotherapy system, wherein performing first pass optimisation comprises:

optimising the set of parameters based on the first reference objective such that the radiotherapy system achieves a first pass achieved value, responsive to the first pass achieved value not meeting the first reference objective:

obtaining a first pass relaxed objective using the first pass achieved value and a first pass relaxation value; and optimising the set of parameters based on the second reference objective, and using the first pass relaxed objective as a constraint, such that the radiotherapy system achieves a further first pass achieved value, performing second pass optimisation, according to the first reference objective and the second reference objective, to determine a further optimised set of parameters, wherein performing second pass optimisation comprises:

responsive to the further first pass achieved value meeting the second reference objective:

optimising the set of parameters based on the second reference objective such that the radiotherapy system achieves a further second pass achieved value; and obtaining a further second pass relaxed objective using the further second pass achieved value and a second pass relaxation value, and determining a configuration of the radiotherapy system using at least the further optimised set of parameters, first pass relaxed objective, and the further second pass relaxed objective.

According to another aspect, there is provided a method for delivering radiation therapy by a radiotherapy system, the method comprising:

receiving a first reference objective and a second reference objective, each reference objective representing a goal to be achieved by the radiotherapy system;

performing first pass optimisation, according to the first reference objective and the second reference objective, to determine a set of parameters, the set of parameters relating to characteristics of radiation to be delivered by the radiotherapy system, wherein performing first pass optimisation comprises:

optimising the set of parameters based on the first reference objective such that the radiotherapy system achieves a first pass achieved value, responsive to the first pass achieved value meeting the first reference objective:

optimising the set of parameters based on the second reference objective, using the first reference objective as a constraint, such that the radiotherapy system achieves a further first pass achieved value, performing second pass optimisation, according to the first reference objective and the second reference objective, to determine a further optimised set of parameters, wherein performing second pass optimisation comprises:

responsive to the first pass achieved value meeting the
    first reference objective:
    optimising the set of parameters based on the first
        reference objective such that the radiotherapy sys-
        tem achieves a second pass achieved value; and
    obtaining a second pass relaxed objective using the
        second pass achieved value and a second pass
        relaxation value, and
    determining a configuration of the radiotherapy system
        using at least the further optimised set of parameters
        and the second pass relaxed objective.

According to another aspect, there is provided a treatment
planning system for delivering radiation therapy by a radio-
therapy apparatus, the treatment planning system compris-
ing a processor configured to:
    receive a reference objective, the reference objective
        representing a goal to be achieved by the radiotherapy
        system;
    perform first pass optimisation, according to the received
        reference objective, to determine a set of parameters,
        the set of parameters relating to characteristics of
        radiation to be delivered by the radiotherapy system,
        wherein performing first pass optimisation comprises:
        optimising the set of parameters such that the radio-
            therapy system achieves a first pass achieved value,
        responsive to the first pass achieved value not meeting
            the reference objective, obtaining a first pass relaxed
            objective using the first pass achieved value and a
            first pass relaxation value,
    determine a configuration of the radiotherapy system
        using the optimised set of parameters and the first pass
        relaxed objective.

In embodiments, the treatment planning system comprises
a processor configured to perform any of the methods above.

According to another aspect, there is provided a com-
puter-readable medium comprising computer-executable
instructions configured to cause a processor to perform any
of the methods above.

In embodiments, the methods are methods of radiation
treatment planning for delivering radiation therapy by a
radiotherapy system.

In some examples, the configuration of the radiotherapy
system may be outputted for delivering radiation by the
radiotherapy system.

The methods are computer-implemented methods, Since
some methods in accordance with examples can be imple-
mented by software, some examples encompass computer
code provided to a general purpose computer on any suitable
carrier medium. The carrier medium can comprise any
storage medium such as a floppy disk, a CD ROM, a
magnetic device or a programmable memory device, or any
transient medium such as any signal e.g. an electrical,
optical or microwave signal. The carrier medium may com-
prise a non-transitory computer readable storage medium.

FIG. 1A shows a block diagram of an optimisation
procedure 100. The optimisation procedure 100 is applicable
to the optimisation of a set of parameters (i.e., one or more
parameters) for a radiotherapy system. The one or more
parameters may be referred to as optimisable parameters, or
as decision variables. Examples of optimisable parameters
comprise parameters that relate to characteristics of radia-
tion to be delivered by the radiotherapy system. For
example, the set of parameters relates to a fluence map. The
fluence map may also be referred to as an intensity profile.
The fluence map may correspond to the weight of the
beamlets (beamlets are described below). An example of a
radiotherapy system will be described below.

The optimisation module 100 comprises an optimiser 107.
Given a model 101 and one or more parameters 103, the
purpose of the optimiser 107 is to provide a set of optimised
parameters 111 that minimise a cost function 102. The
optimizer comprises at least one optimization algorithm
such as a simplex algorithm, a gradient-based algorithm, and
an interior point algorithm, etc, and a combination thereof.
Other optimisation algorithms are also possible. An optimi-
sation algorithm may be executed until a stopping criterion
is reached. For example, a stopping condition may be any
one or more of: a number of iterations being reached, a
convergence criterion being met, and a constraint (such as
constraint 105 described herein) being violated. A constraint
may be a predefined constraint, defined in advance of the
optimisation procedure being performed. Examples of pre-
defined constraints are the clinical and planning constraints
shown in rows a to l of Table 1. Alternatively, a constraint
may be obtained from a previous optimisation procedure.
Examples of optimization are provided in Monaco® Train-
ing Guide, Document ID: LTGMON0530 (Elekta AB). The
optimisation procedure may, for example, correspond to the
optimisation procedure described in European patent appli-
cation publication EP3681600A1.

The model 101 is a representation of the physical prob-
lem. For radiotherapy treatment planning, the model 101
includes, for example, a dose distribution over voxels in a
region. The dose distribution may be the dose at unit fluence.
The region may correspond to an anatomical structure. The
anatomical structure may comprise one or more of: a target,
a region of healthy tissue (known as organs at risk or OARs),
planned target volume (PTV), critical structures, or shell
structures. These structures are determined and/or defined
during a process known as segmentation. Shell structures are
structures generated to tune the dose delivered to the tissue
surrounding the target, and they may be used to control dose
conformality. The dose distribution may be determined by
pencil beam algorithms, convolution based algorithms and/
or Monte Carlo (MC) based algorithms. Further details of
how the dose may be determined are provided in Monaco®
Training Guide, Document ID: LTGMON0530 (Elekta AB).

The one or more parameters 103 are optimisable param-
eters (also referred to as decision variables) for which the
optimiser 107 attempts to find optimum values. The one or
more parameters 103 may be initialised to a predetermined
value. In an example, for IMRT and when the parameters
103 are the weight of beamlets, the parameters 103 may be
initialised to a predetermined weight. Alternatively, the
parameters 103 may be initialised to values determined in a
previous step. For example, when a further optimisation is
performed, the parameters may be initialised to values
determined in a previous optimisation.

A beam may be divided into beamlets where the weight of
each beamlet may be adjusted. A beam may be understood
as a matrix of beamlets. Thus, a beam may be represented by
a plurality of beamlets. The total dose distribution is then the
weighted sum of the contribution of each beamlet at unit
fluence (For example, the dose at a voxel k is given by
$\Sigma x_n \cdot d_{n,k}$, where n is an index for beamlet n, $x_n$ is the weight
of beamlet n, and $d_{n,x}$ is the dose at unit fluence at voxel k
due to beamlet n). By tuning the weight of the beamlets, the
radiation may be modulated. The weight of the beamlets
may be adjusted by adjusting the configuration of a beam
shaping apparatus, such as the part 850 of FIG. 8. For
example, when the beam shaping apparatus is an MLC, the
optimised beamlet weights (and hence the desired dose
distribution) may be implemented by using different aper-
ture shapes of the MLC (also referred to as segments) to shape the delivered radiation. The weight of a beamlet is related to the dose rate. The dose rate refers to how much dose a linac or energy source may deliver per unit time. For a fixed dose rate, the beamlet weight is proportional to the amount of time the beamlet is active. The beamlet may be active, for example by having an opening in the beam shaping apparatus, at a location corresponding to the beamlet, such that radiation may pass through. For example, a higher weight means the beamlet is kept active for a longer time. Thus, the weight of a beamlet is a function of dose rate and/or the duration for which the beamlet is kept active.

The cost function 102 is a mathematical formulation that relates the parameters 103 and the model 101. The cost function may be referred to as an objective function. The cost function 102 relates the dose distribution in the model 101 to a single value (the cost function value 109). For example, when the reference objective is "the mean dose for the bladder is less than 30 Gy", the cost function mathematically formulates and computes the mean dose for the bladder as a function of parameters 103, and compares the achieved mean dose to the reference of 30 Gy. During optimisation, the optimiser 107 seeks parameters that would minimize the difference between the achieved mean dose and the reference mean dose. The cost function value quantifies how close the dose in the model is to a desired value.

The cost function value 109 is value of the cost function 102 when evaluated with the set of optimised parameters. The cost function value 109 is calculated by the optimiser during optimisation. The cost function value 109 may be referred to as a penalty. Optionally, the cost function value 109 is output by the optimiser.

The cost function value 109 represents a penalty for violating an objective or constraint. The penalty is evaluated by the optimiser during optimisation. Optionally, in constrained optimisation, only objectives contribute to the cost function.

The constraint 105 comprise one or more conditions that the optimised parameters 111 must satisfy. The constraint may be a hard constraint (which set conditions that the parameters are required to satisfy) or soft constraint (which have some variable values that are penalised in the cost function if some conditions are not satisfied). Constraints restrict the set of solutions that are obtainable. Constraints are used to define what is physically or clinically acceptable rather than what is mathematically possible. For example, for IMRT, a constraint may be that the weights of the beamlets must be non-negative (since a negative beamlet weight is not possible). Note that the constraint 105 is an optional feature.

The reference objective 104 represents a goal to be achieved. In an example, for IMRT, the reference objective comprises a dose-based objective and/or a volume-based objective. A dose objective may be defined in terms of a dose value (in Gy). An example of a dose objective may be stated as "the average dose to an OAR should be less than or equal to 30 Gy". A volume-based objective may comprise a relative volume or an absolute volume. The relative volume represents a fraction of a volume. For example, the relative volume is a percentage. The absolute volume may be defined in terms of physical dimensions (e.g., in mm, cm, $mm^3$, $cm^3$, etc). An example of a volume based objective may be stated as "at least 90% of the volume of a PTV should meet some criterion". In another example, a reference objective 104 may be stated as "at least X % of a first region receives at least Y Gy". The optimiser 107 may then determine optimised parameters 111 that result in an achieved goal value 113 that is close to the reference objective 104. The reference objective may be referred to as a treatment-planning objective. Note that the reference objective 104 is an optional feature. Additionally and optionally, the reference objective 104 comprises an indication of a cost function 102 to be used. Yet optionally, the reference objective comprises an indication of an anatomical structure to which the goal to be achieved is applicable.

The reference objective is an anatomy specific function that establishes the dose and/or biological response goal. Constraints 105 are anatomy-specific functions that must be met. They may be referred to as hard constraints. When constraints are used together with objectives, constraints are always met, while objectives may not be met (instead, they are goals that the optimiser tries to achieve).

The cost function 102, together with the model 101, the parameters 103, constraints 105 (optional) and reference objective 104 (optional), define the problem to be solved.

The cost function 102, constraints 105, reference objective 104, either alone or in any combination, may be referred to as a treatment-planning objective. The treatment-planning objective may be associated to an anatomical structure. In other words, a treatment-planning objective may comprise any of cost function 102, constraint 105, reference objective 104. An example of a treatment-planning objective may be stated as "97% of the volume of a PTV should receive a dose of at least 30 Gy, using a "Target Penalty" cost function", Other examples of treatment-planning objectives are listed in row m to x in Table.

The optimiser 107 aims to find a set of optimised parameters 111 for which the cost function 102 is minimised. The optimised parameters 111 are an output of the optimiser 107. In an example, when a reference objective 104 is present, the optimiser 107 minimises the difference between the goal value 113 (e.g., the output of the optimiser) and a reference objective 104.

Optionally, the optimiser 107 outputs the cost function value 109. The cost function value 109 is the value of the cost function 102, when evaluated with the optimised parameters 111.

Optionally, the optimiser 107 outputs an achieved goal value 113. The achieved goal value 113 is comparable to the reference objective. An achieved goal value 113 represents a value that has the same units as a given reference objective. The achieved value 113 may be different from the cost function value 109. Unlike the cost function value 109, which may be a number that is an evaluation of the cost function, the achieved value 113 may have a physical meaning. In an example, when the reference objective comprises a dosimetric objective in Gray (Gy), the achieved goal value also relates to a dose (e.g., it has the units of Gy and/or the same physical meaning as the reference objective). In an example, when the reference objective comprises a reference volume and a dose value, the achieved goal value also relates to a reference volume and a dose value (i.e. it has the same physical meaning as the reference objective). As will be described below in relation to Table 1, a reference objective may be DVH-based and may be for a percentage of a volume to receive a predetermined dose. The cost function value 109 may be a number that corresponds to a cost function evaluated with a set of optimised parameters. The achieved goal value 113 would be the achieved percentage of the volume that receives the predetermined dose. In other words, the achieved goal value 113 is comparable to the reference objective.

Figure 1B:
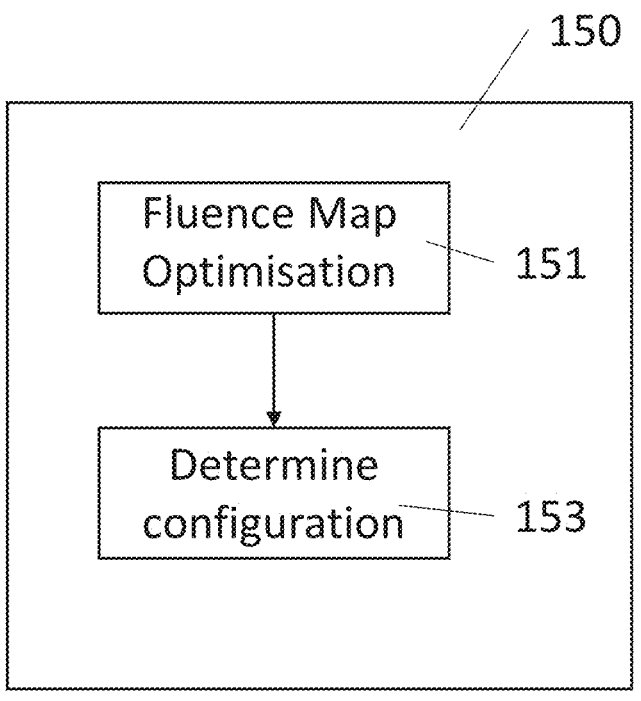
FIG. 1B shows a block diagram of an optimisation procedure applied to IMRT according to an example.

FIG. 1B shows an example of a two-stage optimisation procedure 150 for IMRT. Although this example applies to IMRT, it is noted that optimisation procedure 100 may be applied to other modes of radiotherapy. For example, the optimisation procedure may also be applied to volumetric modulated arc therapy (VMAT).

In IMRT, one or more radiation beams are directed to a tumour. The intensity of each beam profile is non-uniform. The aim of optimisation procedure 150 is to modify the intensity profile such that a high enough dose is delivered to the tumour, while reducing the dose delivered to healthy organs.

The method of optimisation for IMRT 150 comprises two stages. The first stage 151 is fluence map optimisation (FMO) and the second stage 153 is the determination of a configuration of the radiotherapy system. In FMO (stage 151), an optimal fluence map is determined. The optimal fluence map is then used to determine a configuration for the radiotherapy system in stage 2. FMO step 151 will be described next. Step 153 will be described further below.

For fluence optimisation, each beam is divided into a number of beamlets. The contribution of each beamlet, at unit fluence, to voxels is then calculated. Initially, the beamlets may be equally weighted and may contribute equally to the dose distribution. During optimisation, the weight of each beamlet is adjusted such that a cost function is minimised. By multiplying the weight with the contribution of each beamlet at unit fluence and then summing for all beamlets, the full dose distribution may be obtained. The full dose distribution may be compared with any constraints and/or reference objective to determine if the optimised solution is suitable.

The optimisation procedure for FMO may also be expressed as follows. The optimisation procedure for FMO may be performed by the optimisation procedure 100 described herein.

Optimisation comprises minimizing a cost function f(x) by determining suitable values of parameters x based on certain constraints g. For FMO, the parameters x correspond to the weight of the beamlets (x may also be referred to as decision variables, which are the parameters that may be controlled). The output of FMO (Stage 151) comprises parameters x.

The constraints g comprise restrictions. An example of a restriction is a minimum dose at voxels corresponding to a target, or a maximum dose at voxels corresponding to OAR, etc. . . .

In an example, a cost function f(x) is:

$$f(x)=T1+T2+ \ldots +T3$$

where, e.g., $T1=\Sigma x_n \cdot d_n$, where, when x corresponds to weight of a beamlet, $d_n$ represents the dose that each beamlet gives to a voxel at unit intensity. $d_n$ is a non-optimizable parameter (e.g., it may depend on machine configuration and/or properties of the tissue). $d_n$ may be obtained from the model 101 described above. For example, from the model 101, it is known whether a voxel n belongs to a target, an OAR, etc. . . . In an example, the dose $d_n$ may be determined by pencil beam algorithms, convolution based algorithms and/or Monte Carlo (MC) based algorithms. Optionally, dose calculations use pencil beam algorithms or convolution based algorithms (which are fast but have reduced accuracy). Further details of how the dose $d_n$ may be determined are provided in Monaco® Training Guide, Document ID: LTGMON0530 (Elekta AB).

The output of stage 1 may include a dose distribution.

In this example, the cost function f(x) is the sum of the total dose (T1, T2 . . . T3) where each of T1, T2 . . . T3 represent the dose on different structures. Note that alternative formulations of the problem to be solved (e.g. by defining different cost functions or constraints) may be used.

In an example, the requirement for the dose at a target to be above a certain amount may be formulated as a constraint. Alternatively, such a requirement could be formulated as a reference objective.

Step 151 provides a set of optimised parameters (e.g., beamlet weights x) that would provide an optimum intensity map (or fluence map). To be ready for delivery by the radiotherapy system, a further step (step 153) is required to translate each optimised beamlet weight into a configuration of the machine that would deliver the optimum fluence.

Determining a configuration (step 153) is described next.

At step 153, the output from step 151 is turned into a configuration of a radiotherapy system. The configuration is useable by a radiotherapy apparatus (examples of which are described herein) for delivering radiation therapy. For example, the configuration of the radiotherapy system comprises a set of (i.e, one or more) aperture configurations. The shapes and weights of the aperture configurations are selected to meet the same goal as in the first stage. Here, shape refers to a shape of an opening. Each shape may be referred to as a segment. Here, weight refers to the weight of each segment. The weight of a segment is related to the dose rate. For a fixed dose rate, the segment weight is proportional to the amount of time the beam is delivered through the segment. For example, a higher segment weight means a longer delivery time through the segment. Thus, the weight of a segment is a function of dose rate and/or the duration for which the beam is delivered through the segment. Aperture configurations may be realised by a beam shaping apparatus, such as part 850 of FIG. 8. When the beam shaping apparatus is an MLC, the shapes are defined by leaf positions.

An aperture configuration may be referred to as a control point or a segment. The control point and/or segment comprise radiation information (e.g. energy, dose) and geometric information such as gantry angle and leaf position.

The shapes and weights of the apertures may be determined by applying algebraic and trigonometric considerations to the arrangement of the aperture in order to implement the optimised beamlet weights of step 151.

Alternatively, step 153 comprises performing a second stage optimisation procedure to determine an optimised aperture configuration that would implement the optimised fluence pattern determined in step 151. The second stage optimisation procedure may be referred to as aperture optimisation, or aperture refinement.

Aperture optimisation may comprise the following:

Receiving a set of beamlet weights (e.g., from step 151)

Performing optimisation to determine optimised aperture shapes and, optionally, weights.

The optimisation may be performed using an optimisation procedure such as in FIG. 1A, for example. Other optimisation procedures are possible.

When the beam shaping apparatus comprises an MLC, aperture optimisation may comprise:

Receiving a set of beamlet weights from FMO and/or fluence profiles (e.g., from step 151)

Converting the received profile into beamlet widths (the opening between a leaf pair). This results in a segment.

Optimising the weights of the resulting segments.

Optionally, optimising shapes of the resulting segments (using a procedure referred to as segment shape optimisation).

Note that the optimisation steps in step 153 may comprise a calculation of the dose distribution. The dose distribution may be calculated using pencil beam algorithms, convolution-based algorithms and/or Monte Carlo (MC) based algorithms. Optionally, dose calculations in step 153 use MC based algorithms (which are more accurate but computationally expensive).

Further details of aperture optimisation are provided in Monaco® Training Guide, Document ID: LTGMON0530 (Elekta AB).

As will be described herein, in relation to the embodiments of FIG. 2 and FIG. 3, the step of determining a configuration of the radiotherapy system (step 153) is based on at least a set of optimised parameters and a relaxed objective from stage one (step 151). In particular, when step 153 comprises optimisation, the relaxed objective(s) may be used in the formulation of the optimisation problem of step 153. By having more suitable relaxed objective(s), the optimisation problem of step 153 may be improved (e.g, by having improved convergence, or improving the chance that the outcome of step 153 is suitable)

Note that the procedure of FIG. 1B relates to one specific angle. In an approach, a prior step would be to determine the angles from which radiation is to be delivered from. The beam angle optimisation (BAO) procedure is carried out before the procedure of FIG. 1B, the procedure of FIG. 1B is then carried out for each determined angle.

While the example of FIG. 1B relates a two-stage optimisation procedure (FMO at step 151 and determination of a configuration at step 153) for IMRT, it is noted that alternative methods of optimisation, such as Direct Machine Parameter Optimisation (DMPO), may be used instead. In DMPO, the decision variable x corresponds to a parameter of a machine (e.g. an MLC leaf position) that delivers radiation. Yet alternatively, the decision variable x may correspond to any one or more of the following: number of beams, beam angles, a dose per beam, beamlet weights, segment or control point shapes, segment or control point weights, dose-volume histogram information, a dose excess value.

Returning to cost function 102 in optimisation procedure 100, examples of cost functions comprise: Target EUD, Target Penalty, Quadratic Overdose, Quadratic Underdose, Serial, Parallel, Maximum Dose, Overdose DVH, Underdose DVH. The cost functions are briefly defined below. Each cost function offers different calculation methods.

When the cost function comprises any of target penalty, parallel, overdose DVH, and Underdose DVH, the reference objective is a dose value and a relative volume component (e.g. a percentage) or an absolute volume (e.g. in cc).

When the cost function comprises any of Target EUD, quadratic overdose, serial, maximum dose, or conformality, the reference objective is a dose value.

Cost functions such as serial, parallel, quadratic overdose, overdose DVH, or maximum dose aim to limit the dose at an anatomical structure. For example, for these cost functions, a penalty is increased as the achieved dose exceeds a reference dose. The penalty may increase the further the achieved dose is above the reference dose.

Cost functions such as quadratic underdose or underdose DVH aim to increase the dose at an anatomical structure. Cost functions such as Target EUD and Target Penalty aim to increase the dose at a structure. For example, these cost functions are used for target or PTV. For these cost functions, a penalty increases when the achieved dose is lower than a reference dose. The penalty may increase the further the achieved dose is below the reference dose.

Some of the above cost functions also take a unitless number as input. The unitless number (k) is a power law exponent.

The Target EUD cost function defines a structure as a target volume and expresses the probability that a target cell survives a given dose. This cost function requires a prescribed dose as input (i.e. the reference objective for this cost function is a dose value). The prescribed dose, in Gy, is an equivalent uniform dose (EUD). An EUD is a homogenous dose that, if delivered at an anatomical structure, has the same clinical effect that a non-homogenous dose distribution would.

The Target Penalty cost function takes as input a prescribed dose and a minimum volume as input (i.e., the reference objective for this cost function is a dose and a relative volume). The Target Penalty is a quadratic penalty which starts at a threshold dose. It produces steeper dose gradients after a target threshold is met. The Target Penalty is used to define the requirement that at least some fraction of the total anatomical structure volume should receive at least the target dose.

The quadratic overdose (QO) cost function is a cost function used to limit the dose in the structure to which it is applied. The QO may be applied to either targets or OARs. The QO cost function may be used to limit hot spots in a target. The QO cost function takes as input a maximum dose and a root-mean square (RMS) dose excess (i.e. the reference objectives comprises two dose values). The maximum dose defines a dose beyond which a penalty is incurred. The RMS dose excess defines the amount of violation that is acceptable.

The quadratic underdose cost function is a cost function that is applied to a target volume. The quadratic underdose function implements a quadratic penalty. The cost function takes as input a minimum dose in Gy and a dose deficit in Gy (i.e., the reference objective comprises two dose values). The minimum dose is the minimum dose allowable in a target and represents the dose under which a penalty is incurred. The dose deficit is analogous to the RMS dose excess in that it defines the amount of violation from the prescription that is acceptable.

The Serial cost function is generally used with serial OARs. Serial anatomical structures are those where high doses are harmful even if limited to small volumes. Examples include the spinal cord and bowel. This cost function applies large penalties for hot spots even if they are small in volume. The cost function takes as input an EUD in Gy and a power law exponent k (i.e., the reference objective comprises a dose value and a unitless number).

The Parallel cost function is generally used for parallel OARs. Parallel structures are those where very high doses in small volumes are tolerated, if the rest of the organ is spared. Examples are lungs, parotids, kidneys, liver. The cost function takes as input a reference dose in Gy, a mean organ damage (which is a fraction of the volume of the structure that can be sacrificed), and power law exponent k (i.e. the reference objective comprises a dose value, a relative volume, and a unitless number).

The Maximum Dose cost function is effectively a hard barrier that can be applied to target structures or OAR. The Maximum Dose cost function has a penalty that takes effect whenever voxels cross a maximum dose threshold. The cost function takes as input maximum dose in Gy (i.e., the reference objective comprises a dose value)

The Overdose DVH cost function takes as input an objective dose in Gy and a maximum volume (i.e., the reference objective comprises a dose value and a relative volume). This cost function is applied to OARs. The purpose is to keep the volume that receives more than the objective dose below the relative volume.

The Underdose DVH cost function takes as input an objective dose in Gy and a minimum volume (i.e., the reference objective comprises a dose value and a relative volume). This cost function is applied to targets. The purpose is to keep the volume of the target that receives less than the objective dose above the minimum volume.

Further details of the cost functions are provided in Monaco® Training Guide, Document ID: LTGMON0530 (Elekta AB).

Figure 2:
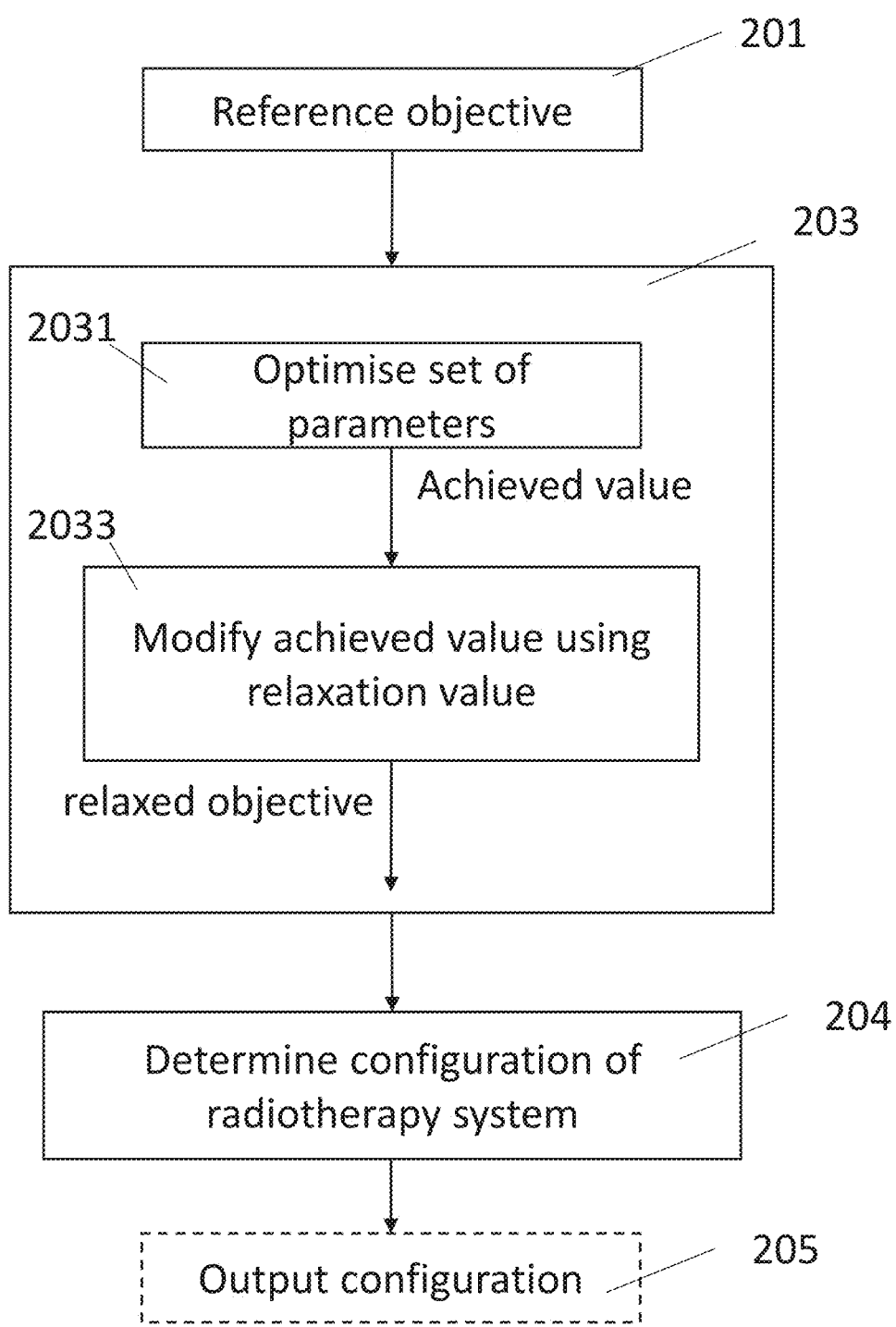
FIG. 2 shows a flow chart of a method of radiotherapy treatment planning according to an embodiment.

FIG. 2 shows a flow chart of a method of radiotherapy treatment planning according to an embodiment. The method is for delivering radiation therapy by a radiotherapy system (such as the radiotherapy system 600 of FIG. 7). The method of FIG. 2 may be performed by the treatment planning system 610 described in relation to FIG. 7.

In step 201, a reference objective is received. The reference objective represents a goal to be achieved when delivering radiation by the radiation system. Optionally, the goal is a clinical goal prescribed by a user (e.g. physician). For example, a reference objective comprises a reference dose and/or a reference volume. The reference objective corresponds to the reference objective 104 described herein.

In step 203, an optimisation procedure is performed to optimise a set of parameters (i.e. one or more parameters). Step 203 may also be referred as a first pass optimisation. Optimisation is performed according to the received reference objective. The aim of the first pass optimisation is to determine values of parameters that would achieve the reference objective. Step 203 comprises steps 2031 and 2033. Optionally, at step 203, a cost function to be used during optimisation is received. The cost function may be provided by a user.

At step 2031, the one or more parameters are optimised and an achieved value (e.g., first pass achieved value) is obtained. The optimisation at step 2031 may be implemented by the optimisation procedure 100 described in FIG. 1A, for example. The first pass achieved value corresponds to the achieved goal value that is achieved by the optimisation procedure of FIG. 1A. The first pass achieved value corresponds to the achieved goal value 113 described in relation to FIG. 1A.

At step 2033, a relaxed objective is obtained using a relaxation value (e.g., a first pass relaxation value). The relaxed objective is obtained by modifying the achieved value using the first pass relaxation value. The relaxed objective may be referred to as a first pass relaxed objective. Optionally, step 2033 is performed in response to the first pass achieved value not meeting the reference objective 201. By the first pass achieved value not meeting the reference objective, it is meant that the first pass achieved value deviates from the reference objective by at least a predetermined amount. The first pass achieved value after step 2031 may differ for a number of reasons. For example, the received reference objective might have been too strict and a set of parameters that would achieve the reference objective might not be available, such that the first pass value at step 2031 does not reach the reference objective. In such a case, the first pass achieved value corresponds to a solution that could be obtained, when trying to achieve the treatment-planning objective. Note that, conversely, by the first pass achieved value meeting the reference objective, it is meant that the first pass achieved value deviates from the reference objective by less than the predetermined amount.

The first pass relaxation value is used (step 2033) to obtain a relaxed objective (e.g., a first pass relaxed objective). The first pass relaxed objective may be less strict than the achieved value. For example, the first pass relaxed objective may be further from the reference objective than the first pass achieved value is from the reference objective. For example, the difference between the first pass relaxed objective and the reference objective may be greater than the difference between the first pass achieved value and the reference objective. For example, when the reference objective relates to a dose value and to an anatomical structure where it is desirable to deliver a sufficiently high dose (e.g., a PTV or target), a relaxed objective may comprise a lower dose value than the achieved value. Conversely, when the reference objective relates to a dose value and to an anatomical structure where it is desirable to reduce dose delivered (e.g., an OAR), a relaxed objective may comprise a larger dose value than for the achieved value.

For example, a reference objective may be "Mean dose to rectum should be ≤30 Gy", but, after first pass optimisation, what is achieved is a minimum mean dose to the rectum of 32 Gy (achieved value=32 Gy). The relaxed objective may then become "Mean dose to rectum should be ≤33 Gy". Here, a relaxation value of 1 Gy is added to the achieved value of 32 Gy to obtain the relaxed objective "Mean dose to rectum should be ≤33 Gy". The relaxed objective is less strict than the achieved value. The relaxed objective is further from the reference objective (33 Gy compared to 30 Gy) than the achieved value is from the reference objective (32 Gy compared to 30 Gy). Although in this example the reference objective and the relaxed objective are defined in terms of a dose, it is noted that the reference objective and relaxed objective could be defined in terms of volume, or in terms of dose and volume.

The first pass relaxed objective may be considered to be an output of the first pass optimisation 203. The first pass relaxed objective is then used in subsequent steps. For example, the first pass relaxed objective is used as a constraint for a subsequent optimisation step. By using the relaxation value to obtain the first pass relaxed objective value, it is meant that the first pass achieved value is modified for use as a first pass relaxed objective. Modifying the achieved value may comprise one or more of multiplying, dividing, adding or subtracting the first relaxation value and the first achieved value to obtain a relaxed objective. The first relaxation value represents the deviation between the first pass relaxed objective and the first pass achieved value.

Additionally and optionally, the first relaxation value is defined as a ratio or a percentage (%). When the first relaxation value is defined as a ratio or a percentage (%), applying a first relaxation value to the first objective value means increasing or decreasing the first objective value by the relaxation value. An example of a first relaxation value is 3%. Other examples of values for the first relaxation include 2%, 5% or 10%.

In step 204 a configuration of the radiotherapy system is determined, based on the set optimised parameters and the first pass relaxed objective from step 203. Step 204 corresponds to step 153 of FIG. 1B.

Additionally and optionally, responsive to the first pass achieved value from step 2031 meeting the reference objective, step 2033 is skipped. The reference objective 201 may then be used in subsequent steps. Reference objective 201 is used instead of the achieved value.

In the first pass, the optimiser may find a solution that is some distance from a reference. Defining a constraint, based on the achieved solution and a relaxation value, and allowing the optimisation procedure to progress to subsequent steps may result in a more accurate solution. This reduces the chances that the optimisation procedure is stopped after the first pass to obtain input from a user (for example, to modify the reference), while also suitably constraining optimisation for subsequent steps.

In step 205, the configuration obtained in step 204 is outputted for use by a radiotherapy system. Step 205 is optional.

An example of a method according to FIG. 2 is described next. In an example, the reference objective is to obtain a dose of less than or equal to 30 Gy. First pass optimisation (step 203) is performed. At step 2031, parameters are optimised and the achieved value (first pass achieved value) may be, for example, 35 Gy. Thus, the first pass achieved value does not meet the reference objective. At step 2033 a relaxation value is applied to the first pass achieved value, to obtain a first pass relaxed objective. The first pass relaxed objective is then 35 Gy+1 Gy=36 Gy, Here a relaxation value of 1 Gy is added to the first pass achieved value of 35 Gy. The first pass relaxed objective is used in subsequent steps 204 and 205.

The purpose of modifying the first pass achieved value using a relaxation value to obtain a first pass relaxed objective is to 'give room' to subsequent steps that use the first pass relaxed objective. In particular, when the first pass relaxed objective is used as a constraint, a broader solution space may be accessed (compared to the case where no relaxation is applied). This may improve the performance of the method.

Figure 3:
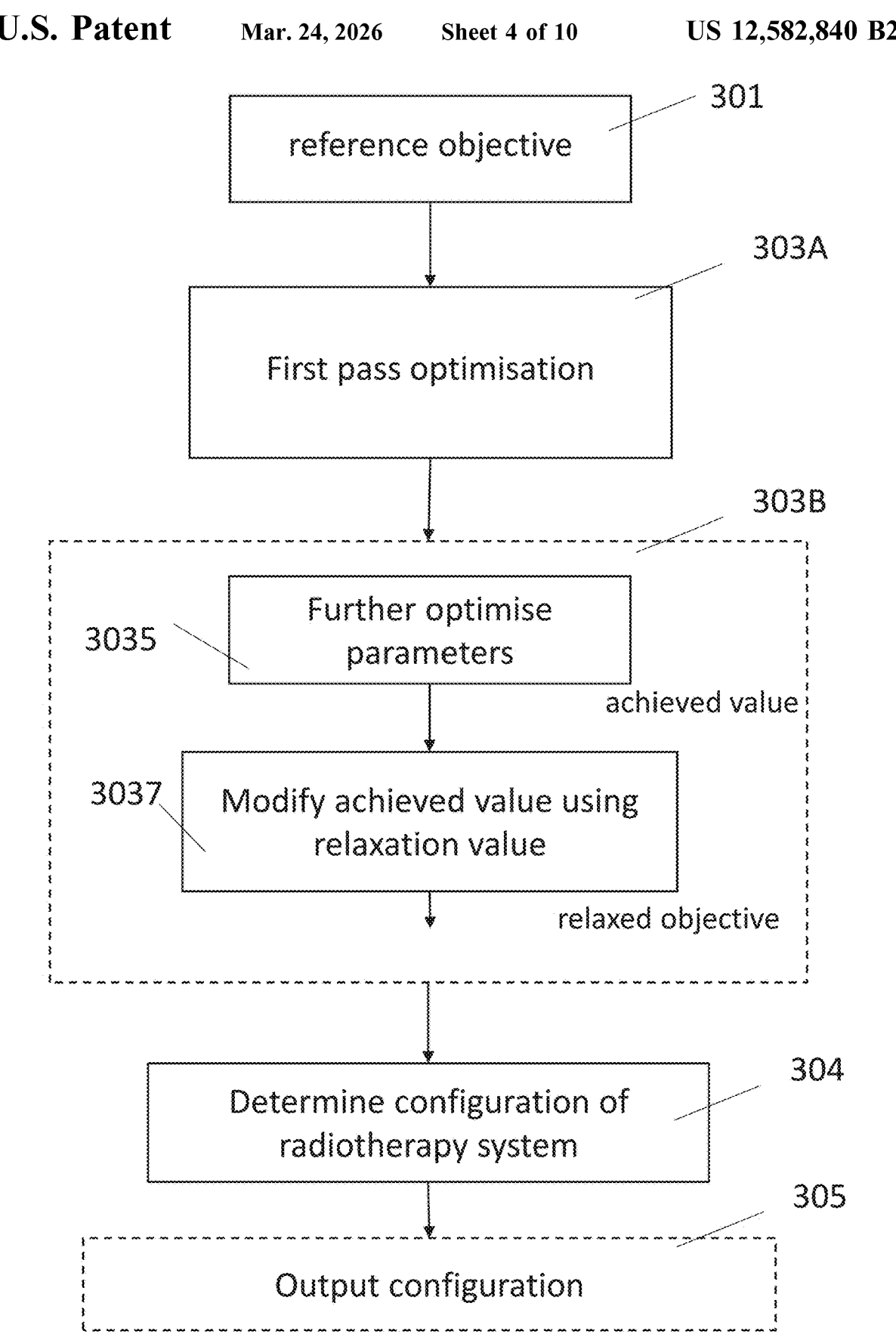
FIG. 3 shows a flow chart of a method of radiotherapy treatment planning according to an embodiment.

FIG. 3 shows a flow chart of a method of radiotherapy treatment planning for delivering radiation therapy by a radiotherapy system according to an embodiment. The method is for delivering radiation therapy by a radiotherapy system (such as the radiotherapy system 600 of FIG. 7). The method of FIG. 3 may be performed by the treatment planning system 610 described in relation to FIG. 7.

The method comprises steps 301, 303A, 303B, 304 and 305. Steps 301, 304 and 305 correspond to steps 201, 204 and 205 of FIG. 2, respectively. Step 303A may be referred to as first pass optimisation and step 303B may be referred to as second pass optimisation. Second pass optimisation (step 303B) is performed after first pass optimisation (step 303A). Step 303B uses the optimised parameters of step 303A as a starting point. Step 303A and step 303B may collectively be referred to as an optimisation procedure.

In step 303A, one or more parameters are optimised. The aim of the optimisation is to determine parameters that would achieve the reference objective received in step 301. Step 303A corresponds to step 203. The output of step 303A comprises a set of optimised parameters, and one or more of a first pass achieved value and a first pass relaxed objective.

At step 303B, the parameters are further optimised. By further optimise, it is meant that the set of optimised parameters from the previous step are used as a starting point for the optimisation procedure. Additionally and optionally, step 303B is performed responsive to the first pass achieved value (from step 303A) meeting the reference objective 301. Alternatively and optionally, the first pass optimisation step 303A corresponds to step 203 of FIG. 2, and, when the first pass achieved value does not meet the reference objective, step 303B is skipped and the first pass relaxed objective from the first pass (step 303A) is used in subsequent steps.

Returning to step 303B, step 303B comprises steps 3035 and 3037. At step 3035, the parameters from step 303A are further optimised to obtain a second pass achieved value.

Optionally, the optimisation may be based on the reference objective 301. The second pass achieved value corresponds to achieved goal value 113 described in relation to FIG. 1A. At step 3037, a second pass relaxation value is used to modify the second pass achieved value from step 3035 to obtain a second pass relaxed objective. The output of step 3035 is a second pass achieved value. The second pass achieved value is analogous to the first pass achieved value obtained in step 2031 of FIG. 2 except that it is obtained from the subsequent optimisation step 3035. Using a second pass relaxation value to modify the second pass achieved value to obtain a second pass relaxation value (step 3037) is analogous to step 2033 of FIG. 2.

At step 304 a configuration of the radiotherapy system is determined, based on the set optimised parameters and the second pass relaxed objective from step 303B. Step 304 corresponds to step 153 of FIG. 1B. In step 305, the configuration obtained in step 304 is outputted for use by a radiotherapy system. Step 305 is optional.

In the methods described in relation to FIG. 2 and FIG. 3, additionally and optionally, the second pass relaxation value is smaller than the first pass relaxation value. This may improve the optimisation procedure further. In steps 303A, the optimiser has already covered a broad solution space. In the second pass optimisation step 3030, the smaller relaxation parameter narrows the solution space and leads to improved optimisation.

Additionally and optionally, the second relaxation value is between 25% to 75% of the first relaxation value. Further optionally, the second relaxation value is 50% of the first relaxation value.

In the methods described in relation to FIG. 2 and FIG. 3, additionally and optionally, the first pass and/or second pass relaxation value is defined relative to (e.g. as a ratio of or a percentage (%) of) a reference objective (which may comprise a dose value) or relative to an achieved value. An example of a relaxation value is 3%. Other examples of values for the relaxation include 2%, 5% or 10%. When the relaxation value is a ratio or percentage, the relaxation may be bounded by a lower value and an upper value. The upper value may be different from the lower value. For example, the relaxation value is 3% (of an achieved value) with 0.6 Gy as lower bound, and 1.2 Gy as upper bound. If the achieved value is 50 Gy, then with 3% relaxation, the achieved value should be relaxed by 50*0.03=1.5 Gy. Since the value of 1.5 Gy exceeds the upper value of 1.2 Gy, the relaxation value is limited the amount of 1.2 Gy. Thus, a relaxed objective may be obtained from the achieved value (50 Gy) and the bounded relaxation value of 1.2 Gy (the 1.5 Gy is limited to the upper value of 1.2 Gy), and the relaxed objective may comprise a dose value of 50+1.2=51.2 Gy. In another example, when the achieved value is 30 Gy, then with 3% relaxation, the achieved value we should be relaxed by 30*0.03=0.9 Gy. Since 0.9 Gy lies is within the bounds (0.6-1.2 Gy), then the relaxed objective may comprise a dose value of 30+0.9=30.9 Gy. The lower value and upper value for the second pass optimisation (step 303B) may differ from the lower value and upper value for the first pass optimisation (step 303A). The purpose of the lower bound and upper bound is to enable the relaxed objective to lie in a more suitable range.

In the methods described in relation to FIG. 2 and FIG. 3, an additional and optional step is to set the first and/or second relaxation value according to the cost function. The purpose is to use a relaxation value that is better suited to the cost function being used (rather than using the same relaxation value for any cost function). This may improve the optimization procedure. Note that, optionally, the cost function is received prior to optimisation steps 203 or 303A. For example, the cost function is received in steps 201 or 301, together with a reference objective.

Additionally and optionally, the relaxation value to use for each cost function may be determined in advance. The relaxation values and their corresponding cost functions may be stored in memory and retrieved for use during the optimisation. Alternatively, the relaxation value is received prior to optimisation steps 203 or 303A. The relaxation value may be obtained together with the cost function. For example, the relaxation value may be user defined.

Returning to the methods illustrated in FIG. 2 and FIG. 3, it is noted that one reference objective is received (step 201 or step 301). However, additionally and optionally, a plurality of reference objectives is received. Each reference objective is tackled in turn.

Figure 4:
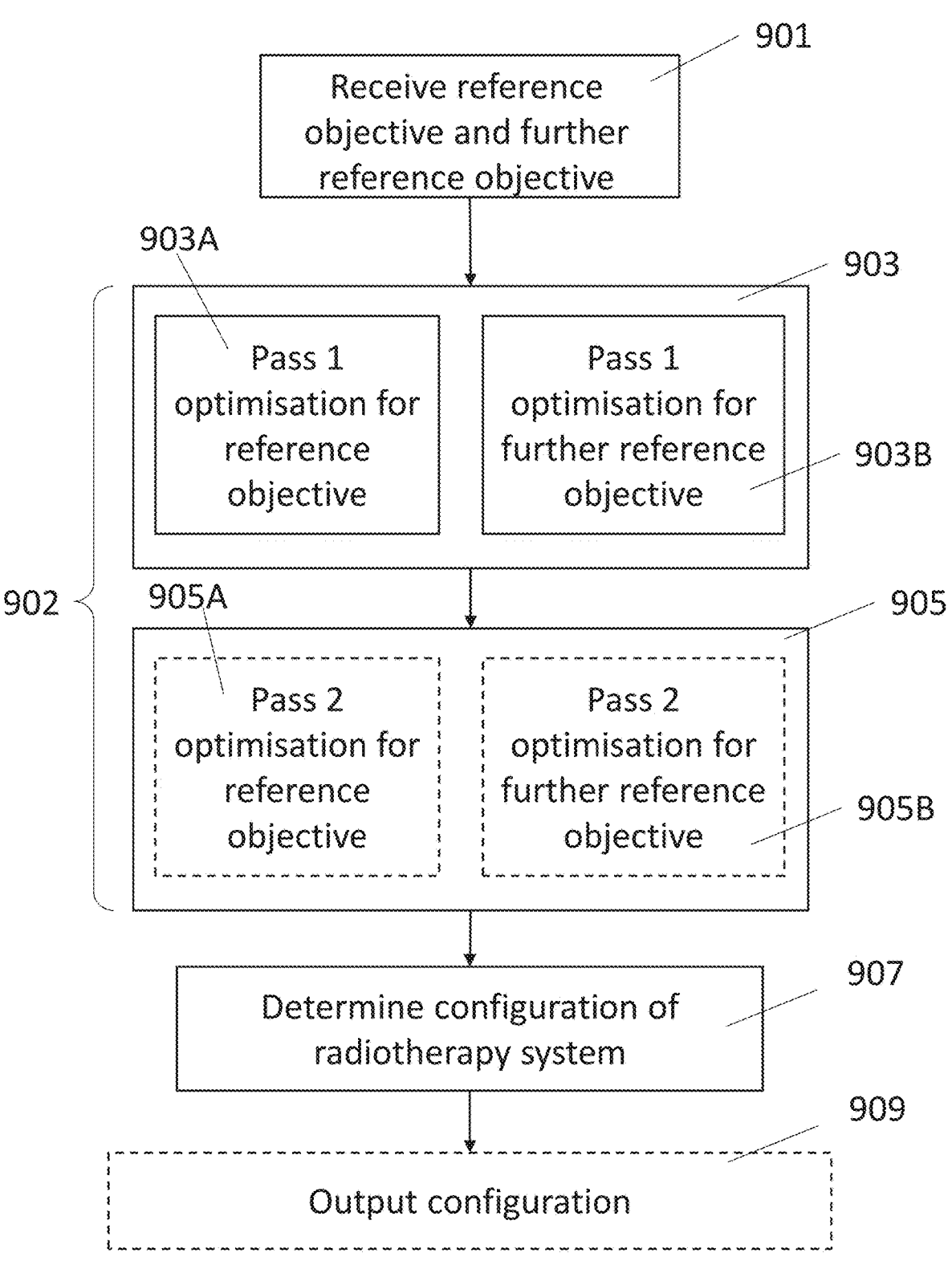
FIG. 4 shows a flow chart of a method of radiotherapy treatment planning according to an embodiment.

FIG. 4 shows a flow chart of a method of radiotherapy treatment planning according to an embodiment. The method is for delivering radiation therapy by a radiotherapy system (such as the radiotherapy system 600 of FIG. 7). The method of FIG. 4 may be performed by the treatment planning system 610 described in relation to FIG. 7.

The method comprises steps 901, 903, 905, 907, and 909. Steps 907 and 909 correspond to steps 204 and 205 respectively. Step 901 is analogous to step 201 or 301 except that a first and a second reference objective are received. The first reference objective may be referred to as a reference objective, and the second reference objective may be referred to as a further reference objective. Step 903 may be referred to as first pass optimisation and step 905 may be referred to as second pass optimisation.

At step 903, each received objective is taken in turn and first pass optimisation (pass 1 optimisation) is performed for each. Step 903 comprises step 903A, where first pass optimisation based on the first reference objective is performed, and step 903B, where first pass optimisation based on the second reference objective is performed.

The aim of step 903A is to determine parameters that would achieve the first reference objective received in step 901. Step 903A is corresponds to step 203 or 303A.

In more detail, step 903A comprises the following steps.

The set of parameters are optimised based on the first reference objective and a first pass achieved value is obtained.

In response to the first pass achieved value not meeting the first reference objective, a first pass relaxed objective is obtained using a first pass relaxation value.

The first pass relaxed objective may be considered to be an output of the first pass optimisation 903A. The first pass relaxed objective may be used in subsequent steps.

After first pass optimisation based on the first objective is performed (step 903A), a further first pass optimisation based on the second reference objective is performed (Step 903B). The aim of step 9033 is to determine parameters that would achieve the second reference objective received in step 901. Step 9033 corresponds to step 203 or 303A.

In more detail, step 903B comprises the following steps.

The set of parameters from step 903A are further optimised based on the second reference objective, and using the first pass relaxed objective obtained from step 903A as a constraint. A further first pass achieved value is obtained. This step is performed when the first pass achieved value from step 903A does not meet the first reference objective.

In response to the first pass achieved value from step 903A meeting the first reference objective, the set of parameters from step 903A are further optimised based on the second reference objective and using the first reference objective from step 901 as a constraint, to obtain a further first pass achieved value. In other words, no relaxation is applied and the first reference objective is used as a constraint in step 903B. A further first pass achieved value is obtained. The further first pass achieved value may be considered an output of step 903B.

In response to the further first pass achieved value in step 903B not meeting the second reference objective, a further first pass relaxed objective is obtained using the first pass relaxation value. Alternatively, in response to the further first pass achieved value in step 903B meeting the second reference objective, no relaxation is applied and the second reference objective may be used as a constraint in subsequent steps.

Returning to step 903, the outputs of step 903 may be considered to be the set of optimised parameters obtained in step 903B. The outputs may also include any one or more of the first pass relaxed objective from step 903A, and the further first pass relaxed objective of step 903B.

Following first pass optimisation (step 903), second pass optimisation is performed at step 905.

At step 905, each received objective from step 901 is taken in turn and second pass optimisation (pass 2 optimisation) is performed for each. Step 905 comprises step 905A, where second pass optimisation based on the first reference objective is performed, and step 905B, where second pass optimisation based on the second reference objective is performed. Note that steps 905A and 905B may be skipped in some circumstances (indicated by dashed lines in FIG. 4), as described herein.

The aim of step 905A is to determine parameters that would achieve the first reference objective received in step 901, starting from the set of optimised parameters obtained from step 903. Step 905A corresponds to step 303B.

In more detail, step 905A comprises the following steps.

In response to the first pass achieved value from step 903A meeting the first reference objective, the set of parameters from step 903 are further optimised based on the first reference objective and a second pass achieved value is obtained. This step corresponds to step 303B.

A second pass relaxation value is used to modify the second pass achieved value to obtain a second pass relaxed objective. The output of step 905A comprises a second pass achieved value and a second pass relaxed objective.

In response to the first pass achieved value from step 903A not meeting the first reference objective, no further optimisation is performed (i.e., step 905A is skipped). Instead, the first pass relaxed objective from step 903 is used in subsequent steps.

After second pass optimisation based on the first objective is performed (step 905A), a further second pass optimisation based on the second reference objective is performed (Step 905B). The aim of step 905B is to determine parameters that would achieve the second reference objective received in step 901. Step 905B corresponds to step 303B.

In more detail, step 905B comprises the following steps.

In response to the further first pass achieved value from step 903B meeting the second reference objective, the set of parameters from step 903B are further optimised based on the second reference objective. A further second pass achieved value is obtained. This step corresponds to step 303B.

The second pass relaxation value is used to modify the further second pass achieved value to obtain a further second pass relaxed objective. The output of step 905B comprises a further second pass achieved value and a further second pass relaxed objective.

In response to the further first pass achieved value from step 903B not meeting the first reference objective, no further optimisation is performed (i.e., step 905B is skipped). Instead, the further first pass relaxed objective from step 903 is used in subsequent steps.

Returning to step 905, the outputs of step 905 may be considered to be the set of optimised parameters obtained in step 905A or 905B (if step 905B has been performed). The outputs may also include any one or more of the second pass relaxed objective from step 905A, and the further second pass relaxed objective of step 905B.

Steps 903 and 905 collectively correspond to a fluence map optimisation step 902. Step 902 corresponds to step 151 of FIG. 1B. From step 902, the following are obtained: a set of optimised parameters from the second pass optimisation (step 905), and either of:

the first pass relaxed objective from step 903A and the further first pass relaxed objective of step 903B;

the first pass relaxed objective from step 903A and the further second pass relaxed objective of step 905B;

the further first pass relaxed objective of step 903B, the second pass relaxed objective from step 905A; OR the second pass relaxed objective from step 905A, and the further second pass relaxed objective of step 905B.

At step 907 a configuration of the radiotherapy system is determined, based on the set optimised parameters and relaxed objectives from step 902, Step 907 corresponds to step 153 of FIG. 1B. In step 909, the configuration obtained in step 907 is outputted for use by a radiotherapy system. Step 909 is optional.

In relation to FIG. 4, it is noted that any of the additional and optional features described in relation to FIG. 2 or 3 are also applicable.

Further in relation to FIG. 4, when the first and/or second relaxation value is based on the cost function, it is noted that the first pass relaxation value used in step 903A may be different from the first pass relaxation value used in step 903B. Similarly, the second pass relaxation value used in step 905A may be different from the second pass relaxation value used in step 905B.

Although FIG. 4 comprises a first and a second objective, the method of FIG. 4 is applicable to three or more reference objectives.

An example with a plurality of objectives is described next. When multiple objectives are present, the objectives may be prioritised and each objective is taken in turn based on its priority.

In a simplified example, for a prostate cancer case, three objectives with different priorities may be defined. There may be some hard constraints to ensure that the tumour receive enough dose.

The objectives may be:

Priority 1: the mean (average) dose to rectum should be less than or equal to 30 Gy.

Priority 2: the mean (average) dose to bladder should be less than or equal to 35 Gy.

Priority 3: the maximal dose to rectum should be less than or equal to 50 Gy.

Using a method analogous to FIG. 4, in pass 1, the optimiser tries to meet each objective one by one based on the priorities (optimiser will try objective with priority 1 first, and then try priority 2, 3 . . . ), and in pass 2, the optimiser only visits the objectives which are met in pass 1 and try to further optimise.

In more detail, in pass 1 (step 903 of FIG. 4):

1) Optimizer tries to reduce the mean dose to rectum (step 903A). After the optimization process is finished, the minimal mean dose for rectum obtained from optimizer is 32 Gy. Then the goal (reference objective: mean dose at 30 Gy) is not achieved. Therefore, this objective is modified using a first pass relaxation value (e.g., first pass relaxation value=1 Gy) to obtain a first pass relaxed objective of 33 Gy (achieved value of 32 Gy+relaxation value 1 Gy). The relaxed objective that that the mean dose to rectum is less than or equal to 33 Gy (32 with 1 Gy relaxation) may then be used in subsequent steps.

2) Optimizer tried to reduce the mean dose to bladder (step 903B), using mean dose to rectum is ≤33 Gy as a constraint (the first pass relaxed objective from the priority 1 optimisation is used as constraint for step 903B). After the optimization process is finished, the mean dose for bladder obtained from optimizer is 26 Gy (further first pass achieved value=26 Gy). Thus, the goal (reference objective: mean dose at 35 Gy) is achieved. Therefore, this reference objective (the mean dose to bladder is less than or equal to 35 Gy) is used in subsequent steps.

3) Optimizer tried to reduce the maximal dose to rectum (Step 903B), using the mean dose to rectum is ≤33 Gy (the first pass relaxed objective from the priority 1 optimisation), and mean dose to bladder ≤35 Gy as a constraints (reference objective of priority 2 optimisation). After the optimization process is finished, the max dose for rectum obtained from optimizer is 45 Gy (further first pass achieved value=45 Gy). Thus, the goal (reference objective: maximal dose at 50 Gy) is achieved. Therefore, this reference objective (maximal dose to bladder is less than or equal to 50 Gy) is used in subsequent steps.

In pass 2 (step 905 of FIG. 4):

1) Priority 1 is skipped because the goal in not achieved in pass 1 (so optimizer will not do anything for this priority anymore). Instead, the first pass relaxed objective (mean dose to rectum is less than or equal to 33 Gy) is used in subsequent steps.

2) Optimizer tried to reduce the mean dose to bladder (step 905B), using mean dose to rectum is ≤33 Gy, and mean dose to bladder ≤35 Gy as constraints. After the optimization process is finished, the mean dose for bladder obtained from optimizer is 28 Gy (second pass achieved value=28 Gy). Thus, second pass achieved value meets the reference objective (30 Gy). A second pass relaxation value (e.g., 0.5 Gy) is used to modify the achieved value to obtain a second pass relaxed objective of the mean dose to bladder is ≤ to 28.5 Gy (=28+0.5 Gy). The relaxed objective of the mean dose to bladder is to 28.5 Gy is used in subsequent steps.

3) Optimizer tried to reduce the maximal dose to rectum, using mean dose to rectum is ≤33 Gy, and mean dose to bladder ≤28.5 Gy (relaxed objective from priority 2 second pass optimisation) as constraints. After the optimization process is finished, the max dose for rectum obtained from optimizer is 47 Gy (further second pass achieved value=47 Gy). Thus, the reference objective is met. The second relaxation value (e.g., 0.5 Gy) is used to modify the achieved value to obtain a second pass relaxed objective of Maximal dose to rectum ≤47.5 Gy (=47+0.5 Gy). The relaxed objective of Maximal dose to rectum ≤47.5 Gy is used in subsequent steps.

The following objectives are obtained from the two passes (step 902):

1) Mean dose to rectum should be less than or equal to 33 Gy

2) Mean dose to bladder should be less than or equal to 28.5 Gy

3) Maximal dose to rectum should be less than or equal to 47.5 Gy.

With reference to the method of FIG. 4, those objectives are used in steps 907 and 909.

An example of a wish-list is described next in relation to Table 1. A wish-list represents the clinical prescription. The clinical prescription may be defined by a user and defines what is desired to be achieved. A wish-list comprises one or more objectives. Here, the objective corresponds to reference objective 104, 201, or 301 described herein. Alternatively (not shown in table 1), the objective may be formulated as a constraint instead. The constraint refers to the constraint 105 described herein.

An example of part of a wish-list for radiotherapy of prostate cancer is described below.

In Table 1, the structure name represents an anatomical structure. The structures are obtained by a process known as segmentation, where contours are drawn on a slice of an MRI image or a CT image to identify the different structures. The contour may be generated manually (e.g., by a physician, dosimetrist, or health care worker) or automatically using an Atlas-based auto-segmentation software.

The wish-list further comprises prioritised objectives (row m to x). The prioritised objectives each correspond to the reference objective described herein. The prioritized objectives comprise: objectives that relate to the dose coverage and conformality of the target (which are the 1st-priority objectives in rows m to q), and objectives that are concerned with dose sparing of the OARs (rows r to y). The prioritised objective may be user-defined priorities.

In Table 1, the "Cost function (parameter values)" relates to the type of cost function to be used. For some cost functions, additional parameters are provided. The 'Goal' refers to a dose or volume to be achieved by the treatment planning system.

For example, at row n, the reference objective is for 97% of the Urethral PRV(a) to achieve a dose of 33.2 Gy. The cost function associated to said reference objective is a 'Target Penalty'.

TABLE 1

Example of a wish-list

| row | Type | Layering order | Structure | Cost function (parameter values) | Goal |
|---|---|---|---|---|---|
| | | | Clinical & Planning Constraints | | |
| a | Clinical | 5 | External | Max Dose | <38 Gy |
| b | Clinical | 6 | Rectum | Parallel (32 Gy, k = 4) | <4.5% |
| c | Clinical | 6 | Rectum | Parallel (28 Gy, k = 4) | <9.5% |
| d | Clinical | 6 | Rectum | Parallel (18 Gy, k = 4) | <34.5% |
| e | Clinical | 8 | Femoral head right | Maximum Dose | <19 Gy |
| f | Clinical | 9 | Femoral head left | Maximum Dose | <19 Gy |
| g | Planning | 1 | Urethral PRV | Quadratic Overdose (35 Gy) | <0.05 Gy |
| h | Planning | 2 | PTV rectum | Quadratic Overdose (34.5 Gy) | <0.10 Gy |
| i | Planning | 3 | PTV bladder | Quadratic Overdose (34.5 Gy) | <0.04 Gy |
| j | Planning | 4 | PTV | Quadratic Overdose (37.3 Gy) | <0.02 Gy |
| k | Planning | 5 | External | Quadratic Overdose (32 Gy) | <0.09 Gy |
| l | Planning | 5 | External | Quadratic Overdose (11.5 Gy) | <0.02 Gy |
| | | | Prioritised Objectives | | |
| m | 1 | 1 | Urethral PRV(a) | Target Penalty (97%) | >33.2 Gy |
| n | 1 | 2 | PTV rectum | Target Penalty (97%) | >33.2 Gy |
| o | 1 | 3 | PTV bladder | Target Penalty (95%) | >33.2 Gy |
| p | 1 | 4 | PTV | Target Penalty (97%) | >35 Gy |
| q | 1 | 4 | PTV | Target Penalty (99.5%) | >33.2 Gy |
| r | 2 | 6 | Rectum | Parallel (28 Gy, k = 4) | <1% |
| s | 3 | 6 | Rectum | Serial (k = 1) | <10% |
| t | 4 | 6 | Rectum | Parallel (18 Gy, k = 4) | <20% |
| u | 5 | 7 | Bladder | Serial (k = 1) | <12 Gy |
| v | 7 | 10 | Penile bulb | Serial (k = 1) | <2 Gy |
| w | 8 | 8 | Femoral head right | Quadratic Overdose (15 Gy) | <0.5 Gy |
| x | 8 | 9 | Femoral head left | Quadratic Overdose (15 Gy) | <0.5 Gy |

The wish-list shown in Table 1 comprises the following.

The wish-list comprises the 'clinical' constraints (rows a to f). The violation of those constraints implies plan rejection. The wish-list further comprises 'planning' constraints (rows g to l). The purpose of 'planning' constraints is to achieve dose conformality and control of potential hotspots.

The clinical constraints and planning constraints are predefined constraints. For example, step 407 of FIG. 4 may refer to checking whether such clinical constraints are met. The purpose of constraints in rows a to l is to limit the dose at the corresponding structures.

For each structure, one or more cost functions and associated goals, each achieving different purposes, is defined. For example, at rows r to t, for the 'Rectum' structure, different cost functions and goals are applied.

In Table 1, the priority refers to the relative priority of the reference objectives. In table 1, the objectives that relate to dose coverage and conformality of the target (which are the 1st-priority objectives in rows m to q) are optimised first, and objectives that are concerned with dose sparing of the OARs (rows r to y) are optimised after, in order of their priorities.

In table 1, the layering order relates to structure volumes that overlap. When structures comprise overlapping voxels, the structure with the higher layering order 'owns' the voxel.

A further example of a wish-list is provided in Naccarato, S., Rigo, M., Pellegrini, R., Voet, P., Akhiat, H., Gurrera, D., De Simone, A., Sicignano, G., Mazzola, R., Figlia, V. and Ricchetti, F., 2022. Automated planning for prostate stereotactic body radiation therapy on the 1.5 T MR-Linac. Advances in radiation oncology, 7(3), p. 100865.

Figure 5:
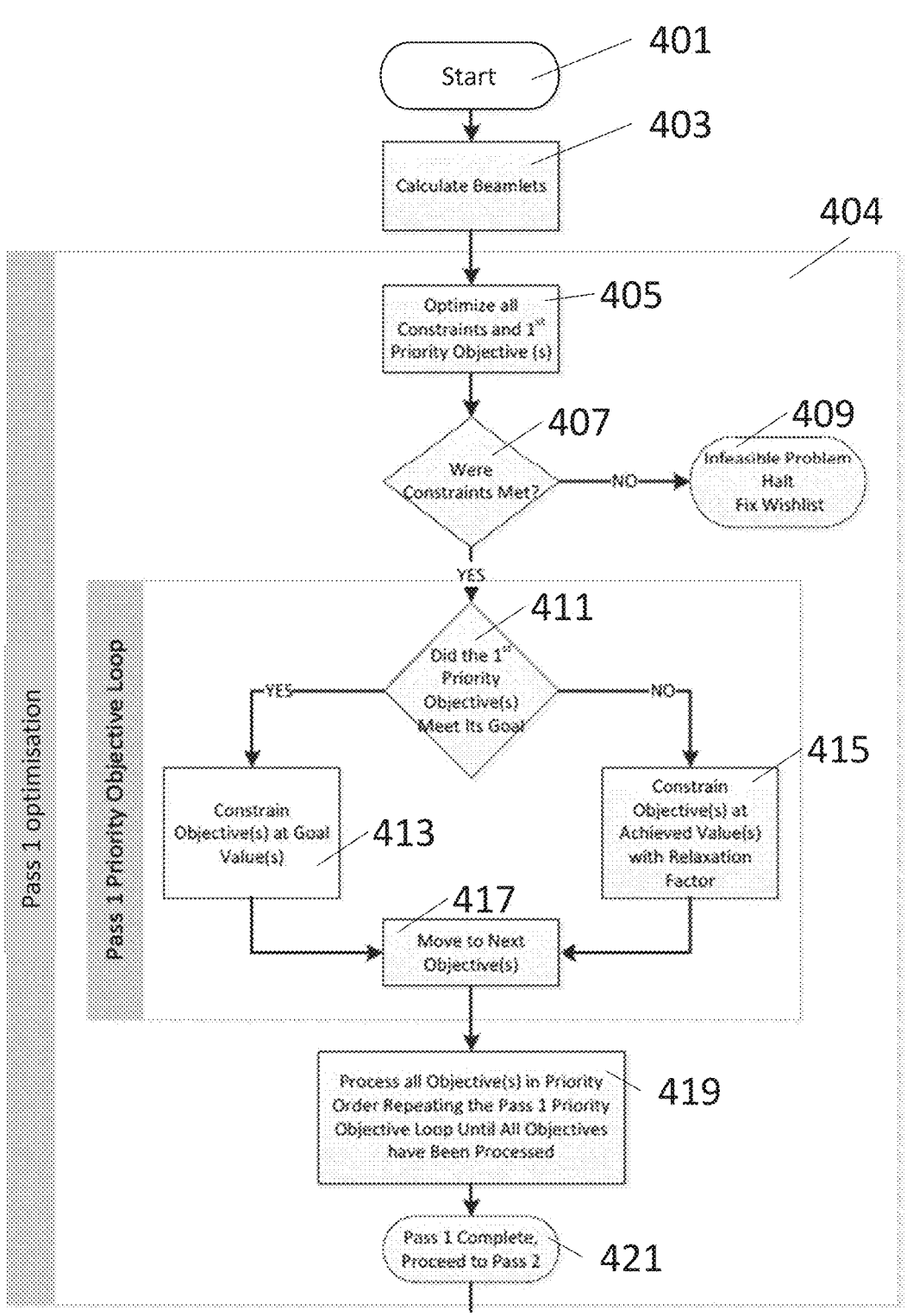
FIG. 5 shows a first part of a flow chart of a method of radiotherapy treatment planning according to an embodiment.

FIG. 5 shows a flow chart of an optimisation procedure for radiotherapy treatment planning according to an embodiment. The method is for delivering radiation therapy by a radiotherapy system (such as the radiotherapy system 600 of FIG. 7). The method of FIG. 5 may be performed by the treatment planning system 610 described in relation to FIG. 7.

At step 401, the optimisation is started.

At step 403, the contribution of each beamlet, at unit fluence, to voxels is calculated.

At step 404, first pass optimisation (pass 1 optimisation) is performed. For performing optimisation, one or more objectives may be obtained. The objectives are prioritised and each objective is considered in turn based on its priority. As described herein, an objective represents a clinical goal to be achieved. An objective may be referred to as a treatment-planning objective. Step 404 comprises steps 405, 407, 409, 411, 413, 415, 417, 419 and 421.

At step 405, optimisation is performed for the first of the one or more objectives. The optimisation is performed taking into account pre-defined constraints. Optimisation step 405 may correspond to the optimisation block 100 described herein. The output of optimisation step 405 is a set of parameters and an achieved value.

At step 407, it is checked whether the output of the optimisation at step 405 met the constraints. If the constraints are not met, at step 409, the procedure is halted. The problem is considered to be infeasible and a user is requested to modify the wish-list. If the constraints can be met, the method proceeds to step 411.

At step 411, it is checked whether the first priority objective met its clinical goal. In other words, it is checked whether the achieved value after optimisation at step 407 meets the first priority objective (reference objective).

When the objective is met (or bettered), at step 413, a constraint is set to the goal value (i.e. the reference objective). The constraint is intended to be used in subsequent steps. For example, subsequent steps comprise first pass optimisation of another objective, second pass of optimisation of the same prioritised objective, or a step subsequent to the optimisation procedure. The second pass is described below in relation to FIG. 6. The purpose of step 413 is to leave room in the solution space for subsequent optimisation.

When the objective is not met, at step 415, the constraint is instead set to a relaxed value, the relaxed value obtained by applying a relaxation value to the achieved value obtained after optimisation at step 405. The relaxed value is intended to be used in subsequent steps (e.g., first pass optimisation of another objective, the second pass of optimisation for the same objective (described below in relation to FIG. 5), or a step subsequent to the optimisation procedure). The relaxed value to the first pass relaxed objective.

At step 417, the next objective is considered.

At step 419, steps 405 to 417 are repeated for all objectives. Thus, for each objective, a first optimisation pass (steps 405 to 417) is carried out and an achieved value is obtained. For each objective, a constraint is obtained. The constraint is set to the goal (reference objective) if the achieved value meets the reference objective (step 413), or to a relaxed value (if goal could not be met)(step 415). For the objectives that were achieving a better result than the goal value (reference objective), the cost function will be revisited in the second pass of the optimization.

Figure 6:
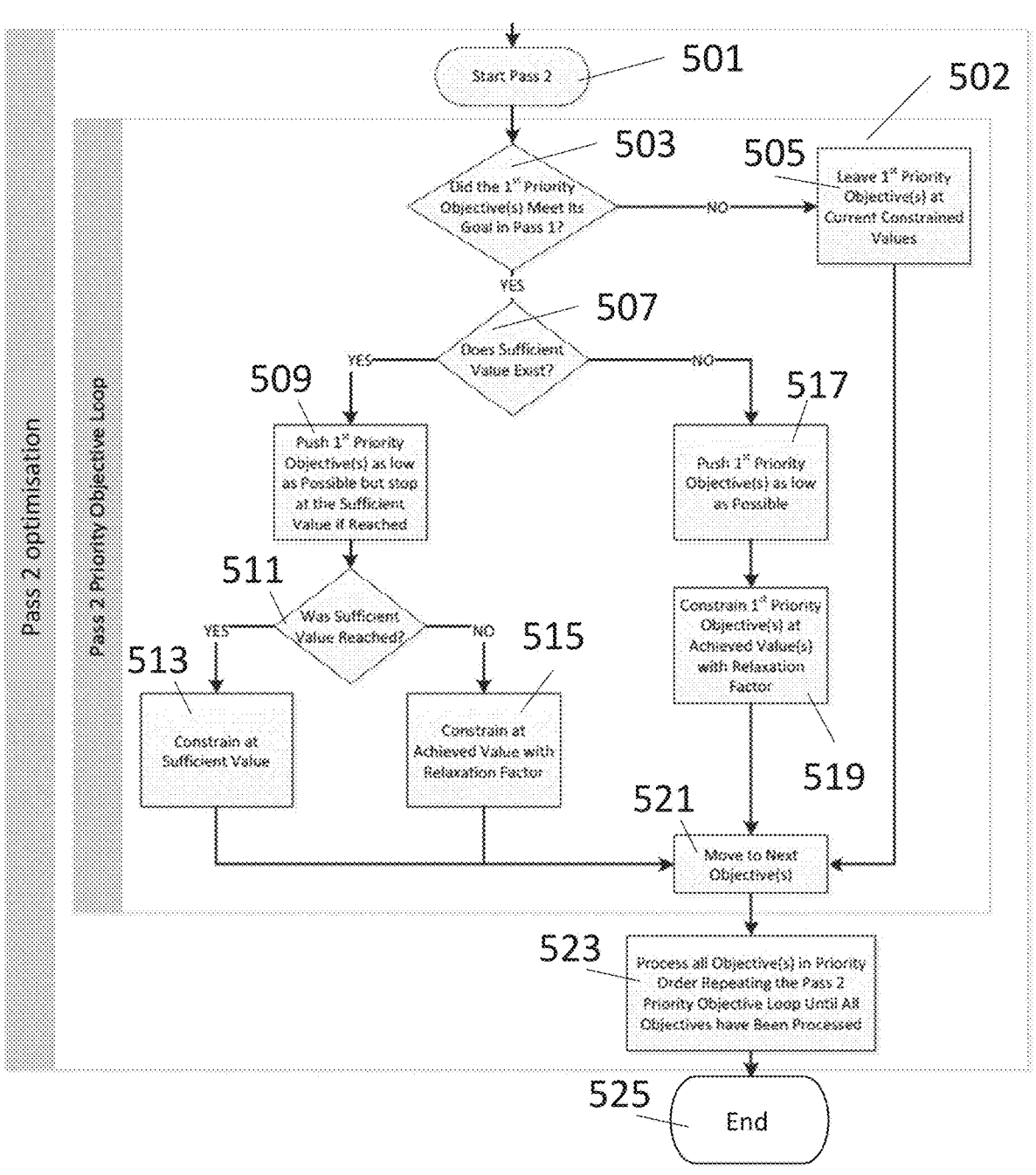
FIG. 6 shows a second part of the method of radiotherapy treatment planning shown in FIG. 4.

At step 421, the first optimisation pass is completed, and the procedure moves to the second optimisation pass described in relation to FIG. 6

FIG. 6 shows a flow chart of an optimisation procedure for radiotherapy treatment planning according to an embodiment. The method shown in FIG. 6 follows the steps carried out in the method of FIG. 5. The flow chart of FIG. 6 depicts second pass optimisation. The method is for delivering radiation therapy by a radiotherapy system (such as the radiotherapy system 600 of FIG. 7). The method of FIG. 6 may be performed by the treatment planning system 610 described in relation to FIG. 7.

At step 501, the second optimisation pass is started. The second pass optimisation starts with the parameters having the values obtained after the first optimisation pass described in FIG. 5. The second pass optimisation utilises the constraints determined in the first pass of FIG. 5 at steps 413 or 415.

At step 502, each objective is considered in turn. Step 502 comprises steps 503 to 521.

At step 503, it is checked whether the first priority objective meets the achieved goal from the first pass. In other words, it is checked whether the achieved value obtained after optimisation at step 405 of FIG. 5 meets the first priority objective (reference objective). When the first priority objective does not meet the achieved goal from the first pass, no further optimisation is carried out for this priority objective. The constraint is kept at its current value at step 505. The constraint is used in subsequent steps. The procedure then moves to the next objective at step 521.

At step 503, when the first priority objective meets the achieved goal from the first pass, the method progresses to step 507.

At step 507, it is checked whether a sufficient value exists. The sufficient value is a pre-determined condition. If the sufficient value exists, the method progresses to step 509, and, if not, to step 517.

A sufficient value is a value that is considered to be good enough from a clinical standpoint. For example, it is desired to spare the parotid, by reducing the mean dose to the parotid gland. The complication probability at the 10 Gy level is very low. This means that trying to reduce the dose to the parotid gland from 10 Gy to 5 Gy may be at the cost of plan complexity (and lead to potential issues with plan QA), and may lead to increased treatment delivery times without any clinical benefit to the patient. By having a sufficient value of 10 Gy, the optimizer is stopped from pushing down further (i.e. the optimiser is prevented from computation once a good enough achieved objective is obtained).

At step 509, further optimisation is performed until the first priority objective (i.e. the achieved value after optimisation) meets or betters the sufficient value. For example, the first priority objective is pushed (i.e. optimisation is performed) as low as possible but stopped at the sufficient value.

At step 511, it is checked if the sufficient value has been reached. If so, at step 513, the sufficient value is used as a constraint (instead of the goal). The constraint is used in subsequent steps.

If the sufficient value is not reached, at step 515, the constraint is set to the achieved value relaxed by a second relaxation value. In other words, a second relaxation value is applied to the achieved value to obtain a second relaxed objective, and said second relaxed objective is used as a constraint in subsequent steps. The method then progresses to step 521.

The purpose of steps 503, 507, 509, 511, 513, and 515, is to revisit the achieved objective value from the first optimisation pass (the achieved objective value having met the reference objective from the first pass) such that the achieved objective value reaches the sufficient value or its lowest possible value (i.e. the achieved objective value is made more suitable for a relaxation value to be applied to obtain a more suitable second relaxed objective value).

Returning to step 507, the method progresses to step 517 when a sufficient value does not exist. At step 517, further optimisation is performed such that first priority objective reaches an optimum (i.e. the achieved value obtained after optimisation is pushed as low as possible). The purpose of steps 503, 507, 517, and 519 is to revisit the achieved objective value from the first optimisation pass (the achieved objective value having met the reference objective from the first pass) such that the achieved objective value reaches its lowest possible value (step 517) (i.e. the achieved objective value is made more suitable for a relaxation value to be applied to obtain a more suitable second relaxed objective value).

At step 519, the constraint is set to the achieved objective value from step 517, relaxed by the second relaxation value. In other words, a second relaxation value is applied to the achieved objective value to obtain a second relaxed objective. The second relaxed objective is used as a constraint in a subsequent steps. The method then progresses to step 521, where the next objective is considered.

At step 523, steps 503 to 521 are repeated for all objectives. Thus, for each objective, a second optimisation pass is carried out and a second pass constraint for a subsequent step is obtained.

At step 525, second pass optimisation is completed.

Figure 7:
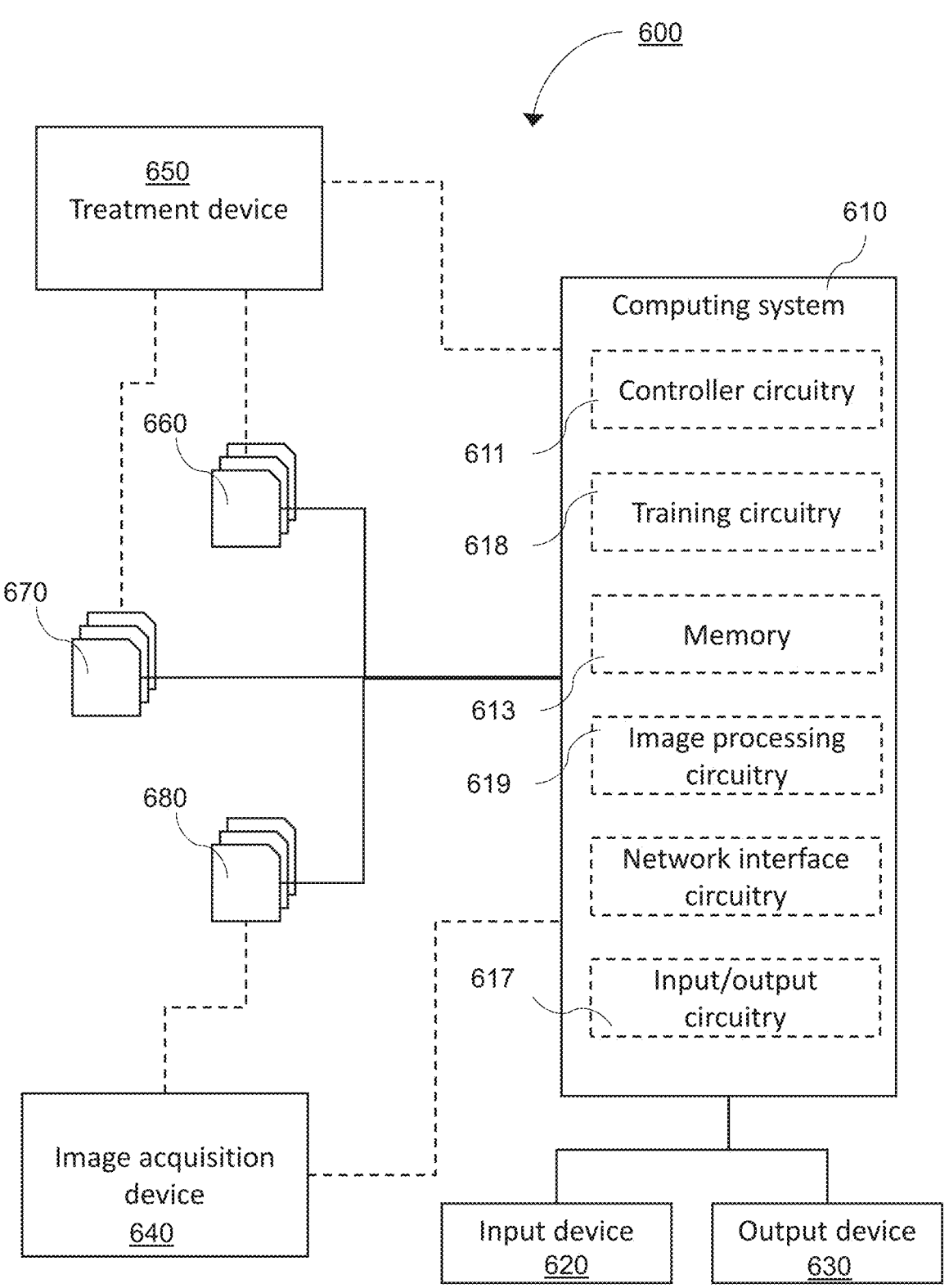
FIG. 7 shows a schematic illustration of a computing device according to an embodiment.

FIG. 7 illustrates a block diagram of an implementation of a radiotherapy system 600. The radiotherapy system 600 comprises a computing system 610 within which a set of instructions, for causing the computing system 610 to perform any one or more of the methods discussed herein, may be executed. The computing system 610 may implement a treatment planning system. The computing system 610 may also be referred to as a computer. The treatment planning system 610 may perform any of the methods described herein. In particular, the methods described herein may be implemented by a processor 611 of the treatment planning system 610.

The computing system 610 shall be taken to include any number or collection of machines, e.g. computing device(s), that individually or jointly execute a set (or multiple sets) of instructions to perform any one or more of the methods discussed herein. That is, hardware and/or software may be provided in a single computing device, or distributed across a plurality of computing devices in the computing system. In some implementations, one or more elements of the computing system may be connected (e.g., networked) to other machines, for example in a Local Area Network (LAN), an intranet, an extranet, or the Internet. One or more elements of the computing system may operate in the capacity of a server or a client machine in a client-server network environment, or as a peer machine in a peer-to-peer (or distributed) network environment. One or more elements of the computing system may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine.

The computing system 610 includes controller circuitry 611 and a memory 613 (e.g., read-only memory (ROM), flash memory, dynamic random access memory (DRAM) such as synchronous DRAM (SDRAM) or Rambus DRAM (RDRAM), etc.). The memory 613 may comprise a static memory (e.g., flash memory, static random access memory (SRAM), etc.), and/or a secondary memory (e.g., a data storage device), which communicate with each other via a bus (not shown).

Controller circuitry 611 represents one or more general-purpose processors such as a microprocessor, central processing unit, accelerated processing units, or the like. More particularly, the controller circuitry 611 may comprise a complex instruction set computing (CISC) microprocessor, reduced instruction set computing (RISC) microprocessor, very long instruction word (VLIW) microprocessor, processor implementing other instruction sets, or processors implementing a combination of instruction sets. Controller circuitry 611 may also include one or more special-purpose processing devices such as an application specific integrated circuit (ASIC), a field programmable gate array (FPGA), a digital signal processor (DSP), network processor, or the like. One or more processors of the controller circuitry may have a multicore design. Controller circuitry 611 is configured to execute the processing logic for performing the operations and steps discussed herein.

The computing system 610 may further include a network interface circuitry 618. The computing system 610 may be communicatively coupled to an input device 620 and/or an output device 630, via input/output circuitry 617. In some implementations, the input device 620 and/or the output device 630 may be elements of the computing system 610. The input device 620 may include an alphanumeric input device (e.g., a keyboard or touchscreen), a cursor control device (e.g., a mouse or touchscreen), an audio device such as a microphone, and/or a haptic input device. The output device 630 may include an audio device such as a speaker, a video display unit (e.g., a liquid crystal display (LCD) or a cathode ray tube (CRT)), and/or a haptic output device. In some implementations, the input device 620 and the output device 630 may be provided as a single device, or as separate devices.

In some implementations, the computing system 610 may comprise image processing circuitry 619. Image processing circuitry 619 may be configured to process image data 680 (e.g. images, or imaging data), such as medical images obtained from one or more imaging data sources, a treatment device 650 and/or an image acquisition device 640. Image processing circuitry 619 may be configured to process, or pre-process, image data. For example, image processing circuitry 619 may convert received image data into a particular format, size, resolution or the like. In some implementations, image processing circuitry 619 may be combined with controller circuitry 611.

Figure 8:
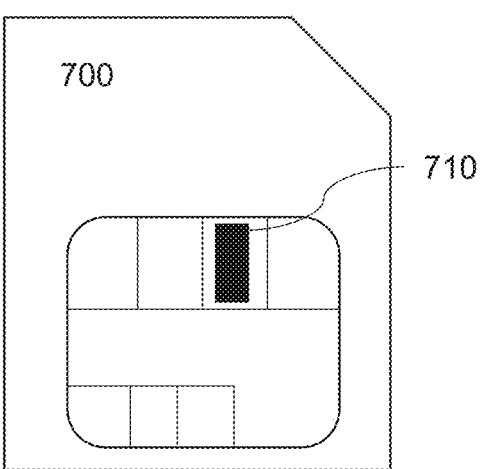
FIG. 8 shows a schematic illustration of a computer-readable medium according to an embodiment.

In some implementations, the radiotherapy system 600 may further comprise an image acquisition device 640 and/or a treatment device 650, such as those disclosed herein in the examples of FIG. 8. The image acquisition device 640 and the treatment device 650 may be provided as a single device. In some implementations, treatment device 650 is configured to perform imaging, for example in addition to providing treatment and/or during treatment. The treatment device 650 comprises the main radiation delivery components of the radiotherapy system, such as beam shaping apparatus 850.

Image acquisition device 640 may be configured to perform positron emission tomography (PET), computed tomography (CT), magnetic resonance imaging (MRI), single positron emission computed tomography (SPECT), x-ray, and the like, Image acquisition device 640 may be configured to output image data 680, which may be accessed by computing system 610. Treatment device 650 may be configured to output treatment data 660, which may be accessed by computing system 610.

Computing system 610 may be configured to access or obtain treatment data 660, planning data 670 and/or image data 680. Treatment data 660 may be obtained from an internal data source (e.g. from memory 613) or from an external data source, such as treatment device 650 or an external database. Planning data 670 may be obtained from memory 613 and/or from an external source, such as a planning database. Planning data 670 may comprise information obtained from one or more of the image acquisition device 640 and the treatment device 650.

The various methods described above may be implemented by a computer program. The computer program may include computer code (e.g. instructions) 710 arranged to instruct a computer to perform the functions of one or more of the various methods described above. For example, the steps of the methods described in relation to FIG. 2, FIG. 3, FIG. 4, FIG. 5 and FIG. 6 may be performed by the computer code 710. The steps of the methods described above may be performed in any suitable order. The computer program and/or the code 710 for performing such methods may be provided to an apparatus, such as a computer, on one or more computer readable media or, more generally, a computer program product 700)), depicted in FIG. 8. The computer readable media may be transitory or non-transitory. The one or more computer readable media 700 could be, for example, an electronic, magnetic, optical, electromagnetic, infrared, or semiconductor system, or a propagation medium for data transmission, for example for downloading the code over the Internet. Alternatively, the one or more computer readable media could take the form of one or more physical computer readable media such as semiconductor or solid state memory, magnetic tape, a removable computer diskette, a random access memory (RAM), a read-only memory (ROM), a rigid magnetic disc, and an optical disk, such as a CD-ROM, CD-R/W or DVD. The instructions 710 may also reside, completely or at least partially, within the memory 613 and/or within the controller circuitry 611 during execution thereof by the computing system 610, the memory 613 and the controller circuitry 611 also constituting computer-readable storage media.

In an implementation, the modules, components and other features described herein can be implemented as discrete components or integrated in the functionality of hardware components such as ASICS, FPGAs, DSPs or similar devices.

A "hardware component" is a tangible (e.g., non-transitory) physical component (e.g., a set of one or more processors) capable of performing certain operations and may be configured or arranged in a certain physical manner. A hardware component may include dedicated circuitry or logic that is permanently configured to perform certain operations. A hardware component may comprise a special-purpose processor, such as an FPGA or an ASiC. A hardware component may also include programmable logic or circuitry that is temporarily configured by software to perform certain operations.

In addition, the modules and components can be implemented as firmware or functional circuitry within hardware devices. Further, the modules and components can be implemented in any combination of hardware devices and software components, or only in software (e.g., code stored or otherwise embodied in a machine-readable medium or in a transmission medium).

Figure 9:
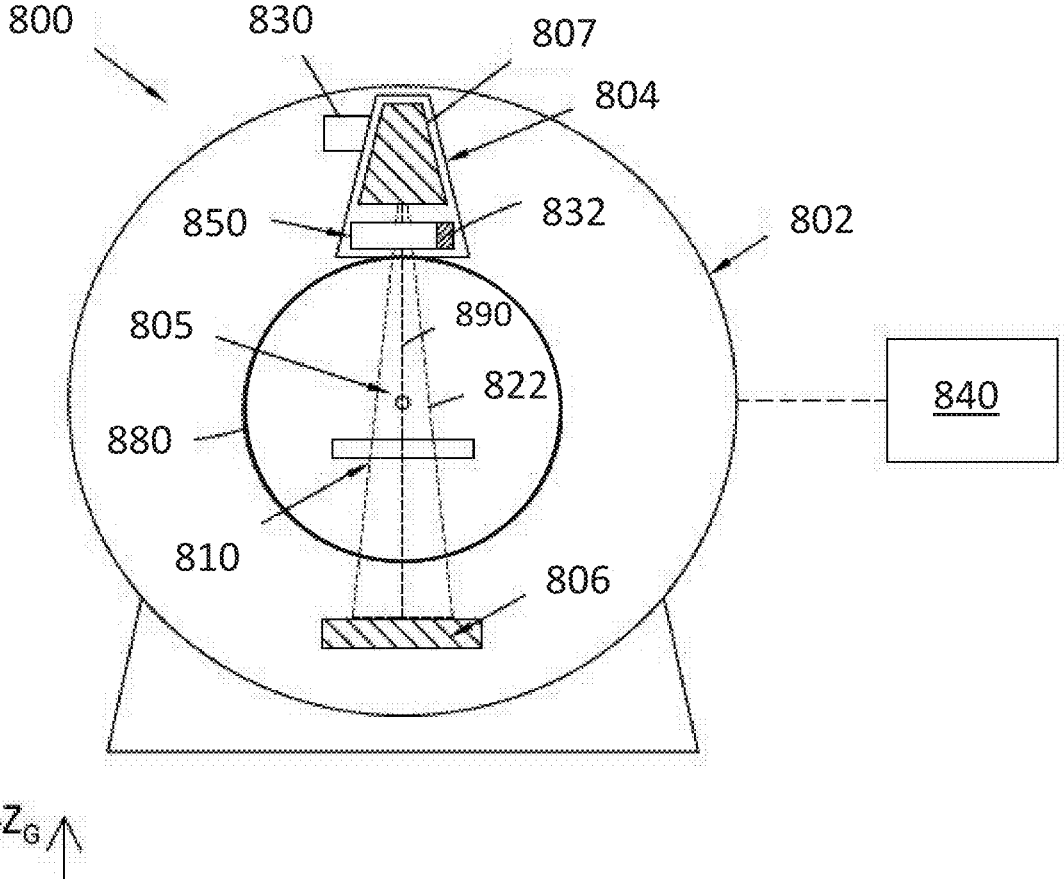
FIG. 9 shows a radiotherapy device or apparatus.

FIG. 9 depicts a radiotherapy apparatus according to the present disclosure. FIG. 9 shows a cross-section through a radiotherapy apparatus 800 comprising a radiation head 804 and a beam receiving apparatus 806, both of which are attached to a gantry 802. The radiation head 804 includes a radiation source 807 which emits a beam of radiation 822. The radiation head 804 also includes a beam shaping apparatus 850 which controls the size and shape of the radiation field associated with the beam.

The beam receiving apparatus 806 is configured to receive radiation emitted from the radiation head 804, for the purpose of absorbing and/or measuring the beam of radiation. In the view shown in FIG. 8, the radiation head 804 and the beam receiving apparatus 806 are positioned diametrically opposed to one another.

The gantry 802 is rotatable, and supports the radiation head 804 and the beam receiving apparatus 806 such that they are rotatable around an axis of rotation 805, which may coincide with the patient longitudinal axis. As shown in FIG. 9, the gantry provides rotation of the radiation head 804 and the beam receiving apparatus 806 in a plane which is perpendicular to the patient longitudinal axis (e.g. a sagittal plane). Three gantry directions XG, YG, ZG can be defined, where the YG direction is perpendicular with gantry axis of rotation. The ZG direction extends from a point on the gantry corresponding to the radiation head, towards the axis of rotation of the gantry. Therefore, from the patient frame of reference, the ZG direction rotates around as the gantry rotates.

FIG. 9 also shows a support surface 810 on which a subject (or patient) is supported during radiotherapy treatment. The radiation head 804 is configured to rotate around the axis of rotation 805 such that the radiation head 804 directs radiation towards the subject from various angles around the subject in order to spread out the radiation dose received by healthy tissue to a larger region of healthy tissue while building up a prescribed dose of radiation at a target region.

The radiotherapy apparatus 800 is configured to deliver a radiation beam towards a radiation isocentre which is substantially located on the axis of rotation 805 at the centre of the gantry 802 regardless of the angle at which the radiation head 804 is placed.

The rotatable gantry 802 and radiation head 804 are dimensioned so as to allow a central bore 880 to exist. The central bore 880 provides opening sufficient to allow a subject to be positioned therethrough without the possibility of being incidentally contacted by the radiation head 804 or other mechanical components as the gantry rotates the radiation head 804 about the subject.

As shown in FIG. 9, the radiation head 804 emits the radiation beam 822 along a beam axis 890 (or radiation axis or beam path), where the beam axis 890 is used to define the direction in which the radiation is emitted by the radiation head. The radiation beam 822 is incident on the beam receiving apparatus 806 which can include at least one of a beam stopper and a radiation detector. The beam receiving apparatus 806 is attached to the gantry 802 on a diametrically opposite side to the radiation head 804 to attenuate and/or detect a beam of radiation after the beam has passed through the subject.

The radiation beam axis 890 may be defined as, for example, a centre of the radiation beam 822 or a point of maximum intensity.

The beam shaping apparatus 850 delimits the spread of the radiation beam 822. The beam shaping apparatus 850 is configured to adjust the shape and/or size of a field of radiation produced by the radiation source. The beam shaping apparatus 850 does this by defining an aperture (also referred to as a window or an opening) of variable shape to collimate the radiation beam 822 to a chosen cross-sectional shape. In this example, the beam shaping apparatus 850 may be provided by a combination of a diaphragm and a multileaf collimator (MLC). Beam shaping apparatus 850 may also be referred to as a bean modifier.

The radiotherapy apparatus 800 may be configured to deliver both coplanar and non-coplanar (also referred to as tilted) modes of radiotherapy treatment. In coplanar treatment, radiation is emitted in a plane which is perpendicular to the axis of rotation of the radiation head 804. In non-coplanar treatment, radiation is emitted at an angle which is not perpendicular to the axis of rotation. In order to deliver coplanar and non-coplanar treatment, the radiation head 804 can move between at least two positions, one in which the radiation is emitted in a plane which is perpendicular to the axis of rotation (coplanar configuration) and one in which radiation is emitted in a plane which is not perpendicular to the axis of rotation (non-coplanar configuration).

In the coplanar configuration, the radiation head is positioned to rotate about a rotation axis and in a first plane. In the non-coplanar configuration, the radiation head is tilted with respect to the first plane such that a field of radiation produced by the radiation head is directed at an oblique angle relative to the first plane and the rotation axis. In the non-coplanar configuration, the radiation head is positioned to rotate in a respective second plane parallel to and displaced from the first plane. The radiation beam is emitted at an oblique angle with respect to the second plane, and therefore as the radiation head rotates the beam sweeps out a cone shape.

The beam receiving apparatus 806 remains in the same place relative to the rotatable gantry when the radiotherapy apparatus is in both the coplanar and non-coplanar modes. Therefore, the beam receiving apparatus 806 is configured to rotate about the rotation axis in the same plane in both coplanar and non-coplanar modes. This may be the same plane as the plane in which the radiation head rotates.

The beam shaping apparatus 850 is configured to reduce the spread of the field of radiation in the non-coplanar configuration in comparison to the coplanar configuration.

The radiotherapy apparatus 800 includes a controller 840 which is programmed to control the radiation source 807, beam receiving apparatus 806 and the gantry 802. Controller 840 may perform functions or operations such as treatment planning, treatment execution, image acquisition, image processing, motion tracking, motion management, and/or other tasks involved in a radiotherapy process.

Controller 840 is programmed to control features of apparatus 800 according to a radiotherapy treatment plan for irradiating a target region, also referred to as a target tissue, of a patient. The treatment plan includes information about a particular dose to be applied to a target tissue, as well as other parameters such as beam angles, dose-histogram-volume information, the number of radiation beams to be used during therapy, the dose per beam, and the like. Controller 840 is programmed to control various components of apparatus 800, such as gantry 802, radiation head 804, beam receiving apparatus 806, and support surface 810, according to the treatment plan.

Hardware components of controller 840 may include one or more computers (e.g., general purpose computers, workstations, servers, terminals, portable/mobile devices, etc.); processors (e.g., central processing units (CPUs), graphics processing units (GPUs), microprocessors, digital signal processors (DSPs), field programmable gate arrays (FPGAs), special-purpose or specially-designed processors, etc.); memory/storage devices such as a memory (e.g., read-only memories (ROMs), random access memories (RAMs), flash memories, hard drives, optical disks, solid-state drives (SSDs), etc.); input devices (e.g., keyboards, mice, touch screens, mics, buttons, knobs, trackballs, levers, handles, joysticks, etc.); output devices (e.g., displays, printers, speakers, vibration devices, etc.); circuitries; printed circuit boards (PCBs); or other suitable hardware. Software components of controller 140 may include operation device software, application software, etc.

The radiation head 804 may be connected to a head actuator 830 which is configured to actuate the radiation head 804, for example between a coplanar configuration and one or more non-coplanar configurations. This may involve translation and rotation of the radiation head 804 relative to the gantry. In some implementations, the head actuator may include a curved rail along which the radiation head 804 may be moved to adjust the position and angle of the radiation head 804. The controller 840 may control the configuration of the radiation head 804 via the head actuator 830.

The beam shaping apparatus 850 includes a shaping actuator 832. The shaping actuator is configured to control the position of one or more elements in the beam shaping apparatus 850 in order to shape the radiation beam 822. In some implementations, the beam shaping apparatus 850 includes an MLC, and the shaping actuator 832 includes means for actuating leaves of the MLC. The beam shaping apparatus 850 may further comprise a diaphragm, and the shaping actuator 832 may include means for actuating blocks of the diaphragm. The controller 840 may control the beam shaping apparatus 850 via the shaping actuator 832.

A treatment plan may comprise positioning information of beam shaping apparatus 850. The positioning information of beam shaping apparatus 850 may comprise information indicating a configuration of one or more elements of beam shaping apparatus 850, such as leaf configuration of an MLC of beam shaping apparatus 850, a configuration of a diaphragm of beam shaping apparatus 850, a configuration of an opening (e.g., window or aperture) of the MLC, and/or the like.

ADDITIONAL NOTES

As described herein, the purpose of an optimiser (or of an optimisation procedure) is to find a set of optimised parameters for which a cost function is minimised. However, it will be understood that, alternatively and equivalently, the purpose of the optimiser (or of the optimisation procedure) may be taken to be to find a set of optimised parameters for which a reward function is maximised.

Unless specifically stated otherwise, as apparent from the following discussion, it is appreciated that throughout the description, discussions utilizing terms such as "receiving", "determining", "comparing", "enabling", "maintaining," "identifying,", "obtaining", "accessing" or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

While certain embodiments have been described, these embodiments have been presented by way of example only, and are not intended to limit the scope of the present disclosure. Indeed, the novel methods and apparatus described herein may be embodied in a variety of other forms; furthermore, various omissions, substitutions and changes in the form of methods and apparatus described herein may be made.

EXAMPLES

Aspects and features of the present disclosure are set forth in the following numbered clauses:

Clause 1A. A method for delivering radiation therapy by a radiotherapy system, the method comprising:
receiving a reference objective, the reference objective representing a goal to be achieved by the radiotherapy system;
performing first pass optimisation, according to the received reference objective, to determine a set of parameters, the set of parameters relating to characteristics of radiation to be delivered by the radiotherapy system, wherein performing first pass optimisation comprises:
optimising the set of parameters to obtain a first pass achieved value,
responsive to the first pass achieved value not meeting the reference objective, obtaining a first pass relaxed objective using the first pass achieved value and a first pass relaxation value, and
determining a configuration of the radiotherapy system using the optimised set of parameters and the first pass relaxed objective.

Clause 2A. The method of clause 1A further comprising:
responsive to the first pass achieved value meeting the reference objective, determining a configuration of the radiotherapy system using the optimised set of parameters and the reference objective.

Clause 1B. A method for radiation treatment planning for delivering radiation therapy by a radiotherapy system, the method comprising:
receiving a reference objective, the reference objective representing a goal to be achieved by the radiotherapy system;
performing an optimisation procedure, according to the received reference objective, to determine a set of parameters, the set of parameters relating to characteristics of radiation to be delivered by the radiotherapy system, wherein the optimisation procedure comprises:
optimising the set of parameters to obtain an achieved value, and
responsive to the achieved value not meeting the reference objective, obtaining a relaxed objective using the achieved value and a relaxation value, and
determining a configuration of the radiotherapy system using the optimised set of parameters and the relaxed objective.

Clause 2B. The method of clause 1B further comprising:
responsive to the first pass achieved value meeting the reference objective, determining a configuration of the radiotherapy system using the optimised set of parameters and the reference objective.

Clause 3B. The method of claim 1B or 2B wherein performing the optimisation procedure comprises:
performing first pass optimisation, first pass optimisation comprising:
optimising the set of parameters to obtain a first pass achieved value, and
responsive to the first pass achieved value not meeting the reference objective, obtaining a first pass relaxed objective using the first pass achieved value and a first pass relaxation value, and
determining a configuration of the radiotherapy system using the optimised set of parameters and the first pass relaxed objective.

Clause 3. The method of clause 1A, 2A, 1B or 2B, wherein determining a configuration of the radiotherapy system using the optimised set of parameters and the first pass relaxed objective comprises:
performing a further optimisation procedure using the relaxed objective or first-pass relaxed as an objective or a constraint.

Clause 4. The method according to clause 1A, 1B, or clause 3 when dependent upon clauses 1A or 1B, further comprising:
performing second pass optimisation, performing second pass optimisation comprising:
responsive to the first pass achieved value meeting the reference objective, further optimising the set of parameters, according to the received reference objective, to obtain a second pass achieved value, and
obtaining a second pass relaxed objective using the second pass achieved value and a second pass relaxation value, and
determining a configuration of the radiotherapy system using the further optimised set of parameters and the second pass relaxed objective.

Clause 5. The method of clause 4, wherein determining a configuration of the radiotherapy system using the further optimised set of parameters and the second pass relaxed objective comprises:
performing an optimisation procedure using the second relaxed treatment-planning objective as an objective or a constraint.

Clause 6. The method of any preceding clause, wherein the set of parameters are related to the fluence pattern of the radiation to be delivered.

Clause 7. The method of clause 6 wherein the set of parameters comprises the weight of beamlets.

Clause 8. The method of any preceding clause wherein determining a configuration of the radiotherapy system comprises determining an arrangement of a beam shaping apparatus.

Clause 9. The method of clause 8 wherein the beam shaping apparatus is a multileaf collimator (MLC).

Clause 10. The method of any preceding clause, wherein the first pass relaxation value and/or second pass relaxation value is automatically set according to a cost function.

Clause 11. The method of any preceding clause, wherein the reference objective comprises any of a cost function, reference dose, and/or reference volume.

Clause 12. The method of clause 11 wherein, when the reference objective comprises a reference dose, the cost function comprises any of: a Maximum dose cost function, a Mean dose cost function, a Serial cost function, and/or an equivalent uniform dose (EUD) cost function.

Clause 13. The method of clause 11 wherein, when the reference objective comprises a reference volume, the cost function comprises any of: a Dose Volume Histogram (DVH) based cost function, a Target Penalty cost function or a Parallel cost function Clause 14. The method of any preceding clause, wherein the reference objective relates to any one or more of: a region of interest, a shell, a planned target volume (PV), a critical structure, and an organ at risk.

Clause 15. The method of any preceding clause, wherein the first/second pass relaxation value is obtained relative to the first/second pass achieved value, and further bounded by a lower value and an upper value.

Clause 16. The method of any preceding clause, wherein the second relaxation value is smaller than the first relaxation value.

Clause 17. The method of clause 16, wherein the second relaxation value is between 25% to 75% of the first relaxation value.

Clause 18. A method for delivering radiation therapy by a radiotherapy system, the method comprising:
receiving a first reference objective and a second reference objective, each reference objective representing a goal to be achieved by the radiotherapy system;
for each reference objective, sequentially optimising the set of parameters according to any preceding clause; and, determining a configuration of the radiotherapy system using the sequentially optimised set of parameters and the first and second reference objectives.

Clause 19. A method for delivering radiation therapy by a radiotherapy system, the method comprising:
receiving a first reference objective and a second reference objective, each reference objective representing a goal to be achieved by the radiotherapy system;
performing first pass optimisation, according to the first reference objective and the second reference objective, to determine a set of parameters, the set of parameters relating to characteristics of radiation to be delivered by the radiotherapy system, wherein performing first pass optimisation comprises:
optimising the set of parameters based on the first reference objective to obtain a first pass achieved value,
responsive to the first pass achieved value not meeting the first reference objective:
obtaining a first pass relaxed objective using the first pass achieved value and a first pass relaxation value; and
optimising the set of parameters based on the second reference objective, and using the first pass relaxed objective as a constraint, to obtain a further first pass achieved value,
performing second pass optimisation, according to the first reference objective and the second reference objective, to determine a further optimised set of parameters, wherein performing second pass optimisation comprises:
responsive to the further first pass achieved value meeting the second reference objective:

optimising the set of parameters based on the second reference objective to obtain a further second pass achieved value; and
obtaining a further second pass relaxed objective using the further second pass achieved value and a second pass relaxation value, and
determining a configuration of the radiotherapy system using at least the further optimised set of parameters, first pass relaxed objective, and the further second pass relaxed objective.

Clause 20. A method for delivering radiation therapy by a radiotherapy system, the method comprising:
receiving a first reference objective and a second reference objective, each reference objective representing a goal to be achieved by the radiotherapy system;
performing first pass optimisation, according to the first reference objective and the second reference objective, to determine a set of parameters, the set of parameters relating to characteristics of radiation to be delivered by the radiotherapy system, wherein performing first pass optimisation comprises:
optimising the set of parameters based on the first reference objective to obtain a first pass achieved value,
responsive to the first pass achieved value meeting the first reference objective:
optimising the set of parameters based on the second reference objective, using the first reference objective as a constraint, to obtain a further first pass achieved value,
performing second pass optimisation, according to the first reference objective and the second reference objective, to determine a further optimised set of parameters, wherein performing second pass optimisation comprises:
responsive to the first pass achieved value meeting the first reference objective:
optimising the set of parameters based on the first reference objective to obtain a second pass achieved value; and
obtaining a second pass relaxed objective using the second pass achieved value and a second pass relaxation value, and,
determining a configuration of the radiotherapy system using at least the further optimised set of parameters and the second pass relaxed objective.

Clause 21. A treatment planning system for delivering radiation therapy by a radiotherapy apparatus, the treatment planning system comprising a processor configured to:
receive a reference objective, the reference objective representing a goal to be achieved by the radiotherapy system;
perform first pass optimisation, according to the received reference objective, to determine a set of parameters, the set of parameters relating to characteristics of radiation to be delivered by the radiotherapy system, wherein performing first pass optimisation comprises:
optimising the set of parameters to obtain a first pass achieved value,
responsive to the first pass achieved value not meeting the reference objective, obtaining a first pass relaxed objective using the first pass achieved value and a first pass relaxation value, and determine a configuration of the radiotherapy system using the optimised set of parameters and the first pass relaxed objective.

Clause 22. The treatment planning system of clause 21, wherein the processor is configured to perform any of the methods above.

Clause 23. A computer-readable medium comprising computer-executable instructions configured to cause a processor to perform any of the methods above.

Clause 24. The methods of any preceding clause, wherein the methods are methods of radiation treatment planning for delivering radiation therapy by a radiotherapy system.

What is claimed is:

1. A method for radiation treatment planning for delivering radiation therapy by a radiotherapy system, the method comprising:

receiving a reference objective, the reference objective representing a goal to be achieved by the radiotherapy system;

performing an optimization procedure, according to the received reference objective, to determine a set of parameters, the set of parameters relating to characteristics of radiation to be delivered by the radiotherapy system, wherein the optimization procedure comprises:

optimizing the set of parameters to obtain an achieved value;

responsive to the achieved value not meeting the reference objective, obtaining a relaxed objective using the achieved value and a relaxation value, and setting the relaxed objective as a constraint; and determining a configuration of the radiotherapy system using the optimized set of parameters and the relaxed objective as a constraint.

2. The method of claim 1 further comprising:

responsive to the achieved value meeting the reference objective, determining a configuration of the radiotherapy system using the optimized set of parameters and the reference objective.

3. The method of claim 1 wherein performing the optimization procedure comprises:

performing a first pass optimization, the first pass optimization comprising:

optimizing the set of parameters to obtain a first pass achieved value;

responsive to the first pass achieved value not meeting the reference objective, obtaining a first pass relaxed objective using the first pass achieved value and a first pass relaxation value; and determining a configuration of the radiotherapy system using the optimized set of parameters and the first pass relaxed objective.

4. The method of claim 3 wherein performing the optimization procedure further comprises:

performing a second pass optimization, the second pass optimization comprising:

responsive to the first pass achieved value meeting the reference objective, further optimizing the set of parameters, according to the received reference objective, to obtain a second pass achieved value;

obtaining a second pass relaxed treatment-planning objective using the second pass achieved value and a second pass relaxation value; and determining a configuration of the radiotherapy system using the further optimized set of parameters and the second pass relaxed treatment-planning objective.

5. The method of claim 4, wherein determining a configuration of the radiotherapy system using the further optimized set of parameters and the second pass relaxed treatment-planning objective comprises:

performing a further optimization procedure using the second pass relaxed treatment-planning objective as an objective or a constraint.

6. The method of claim 4, wherein the second pass relaxation value is smaller than the first pass relaxation value.

7. The method of claim 1, wherein the set of parameters is related to a fluence pattern of the radiation to be delivered.

8. The method of claim 7 wherein the set of parameters comprises a weight of beamlets.

9. The method of claim 1 wherein determining a configuration of the radiotherapy system comprises determining an arrangement of a beam shaping apparatus.

10. The method of claim 9 wherein the beam shaping apparatus is a multileaf collimator (MLC).

11. The method of claim 1, wherein the relaxation value is automatically set according to a cost function.

12. The method of claim 1, wherein the reference objective comprises any of a cost function, a reference dose, and/or a reference volume.

13. The method of claim 12 wherein, when the reference objective comprises a reference dose, the cost function comprises any of: a maximum dose cost function, a mean dose cost function, a serial cost function, and/or an equivalent uniform dose (EUD) cost function.

14. The method of claim 12 wherein, when the reference objective comprises a reference volume, the cost function comprises any of: a Dose Volume Histogram (DVH) based cost function, a Target Penalty cost function or a Parallel cost function.

15. The method of claim 1, wherein the reference objective relates to any one or more of: a region of interest, a shell, a planned target volume (PTV), a critical structure, and an organ at risk.

16. The method of claim 1, wherein the relaxation value is determined relative to the achieved value and further bounded by a lower value and an upper value.

17. A treatment planning system for delivering radiation therapy by a radiotherapy apparatus, the treatment planning system comprising a processor configured to:

receive a reference objective, the reference objective representing a goal to be achieved by the radiotherapy apparatus;

perform optimization, according to the received reference objective, to determine a set of parameters, the set of parameters relating to characteristics of radiation to be delivered by the radiotherapy apparatus, wherein performing optimization comprises:

optimizing the set of parameters to obtain an achieved value;

responsive to the achieved value not meeting the reference objective, obtaining a relaxed objective using the achieved value and a relaxation value, and setting the relaxed objective as a constraint; and determine a configuration of the radiotherapy apparatus using the optimized set of parameters and the relaxed objective as a constraint.

18. A non-transitory computer-readable medium comprising computer-executable instructions configured to cause a processor to:

receive a reference objective, the reference objective representing a goal to be achieved by a radiotherapy system; and perform an optimization, according to the received reference objective, to determine a set of parameters, the set of parameters relating to characteristics of radiation to be delivered by the radiotherapy system, wherein performing the optimization comprises:

optimizing the set of parameters to obtain an achieved value;

responsive to the achieved value not meeting the reference objective, obtaining a relaxed objective using the achieved value and a relaxation value, and setting the relaxed objective as a constraint; and determine a configuration of the radiotherapy system using the optimized set of parameters and the relaxed objective as a constraint.

* * * * *